United States Patent [19]
Maurel

[11] Patent Number: 5,674,700
[45] Date of Patent: Oct. 7, 1997

[54] METHOD FOR THE DETECTION AND/OR ASSAY OF HORMONES, AND ANTIBODIES WHICH CAN BE USED IN THE SAID DETECTION METHOD

[75] Inventor: Marie-Christine Maurel, Tours, France

[73] Assignees: Institut National de la Recherche Agronomique; Centre National de la Recherche Scientifique, both of Paris, France

[21] Appl. No.: 952,866

[22] PCT Filed: May 30, 1991

[86] PCT No.: PCT/FR91/00427

§ 371 Date: Jan. 29, 1993

§ 102(e) Date: Jan. 29, 1993

[87] PCT Pub. No.: WO91/19195

PCT Pub. Date: Dec. 12, 1991

[30] Foreign Application Priority Data

Jun. 1, 1990 [FR] France ................... 90 06863

[51] Int. Cl.$^6$ .................................. G01N 33/543
[52] U.S. Cl. .............. 435/7.94; 435/7.92; 435/7.93; 435/7.95; 435/962; 435/963; 435/967; 435/975; 436/518; 530/387.1
[58] Field of Search ................... 435/7.92, 7.93, 435/7.94, 7.95, 967, 962, 963, 975; 436/518; 530/387.1

[56] References Cited

U.S. PATENT DOCUMENTS

| | | | |
|---|---|---|---|
| 3,991,174 | 11/1976 | Grundman | 436/530 |
| 4,002,532 | 1/1977 | Weltman et al. | 435/7.95 |
| 4,094,963 | 6/1978 | Saxena | 436/504 |
| 4,559,145 | 12/1985 | Hou | 210/679 |
| 4,935,147 | 6/1990 | Ullman et al. | 435/2 |

FOREIGN PATENT DOCUMENTS

| | | |
|---|---|---|
| 98590 | 1/1984 | European Pat. Off. . |
| 193881 | 9/1986 | European Pat. Off. . |

OTHER PUBLICATIONS

R. Bergland et al, "Adrenocorticotropic Hormone may be Transported Directly from the Pituitary to the Brain" Science 210:541–543, 1980.

Schnall, A. M., et al. "Pituitary Cushing's diesease without adenoma." Acta Endocrinologica 94:297–303, 1980.

Boscato, L. M., et al. "Incidence and Specificity of Interference in Two-Site Immunoassays." Clinicial Chemistry 32(8)1491–5, 1986.

Wentworth, B. C. et al. "A Radioimmunoassay for Turkey Leutinizing Hormone," General and Comparitive Endocrinology 29:119–27, 1976.

Fujii, K. et al. "An improved enzyme–linked immunosorbent assay of anti–collagen antibodies in human serum." Journal of Immunological Methods 124:63–70, 1989.

Tijssen, P. Practice and Theory of Enzyme Immunoassays. Laboratory Techiques in Biochemistry and Molecular Biology, vol. 15, New York Elsevier, 1985. pp. 43–64, 96–115, 340–343.

Baenziger, S. U. et al. Pituitary glycoprotein hormone oligosaccharides: Structure, synthesis & function of the asparagine–linked oligosaccharides on lutropin, follitropin and thyrotropin. Biochimica et Biophysica Acta 947:287–306, 1988.

Voller, A., et al. Enzyme–linked Immunosorbent assay. In: Manual of Clinical Laboratory Immunology, 3rd Ed. Washington, D.C.: American Society for Microbiology, 1986, pp. 99–109.

R.L. Sutherland, et al, "Macropod marsupal leiteinizing hormone: validation of assay procedure and changes in concentration in plasma during theoestrus cycle in the femal tamar wallaby (*Macropus eugenii*)". Journal of Endocrinology 86:1–12, 1980.

P.E. Garrett, "Troubleshooting Immunoassays", *Journal of Clinical Immunoassay*, vol. 12, No. 1, Spring 1989, pp. 18–20.

Primary Examiner—Christine M. Nucker
Assistant Examiner—Jeffrey Stucker
Attorney, Agent, or Firm—Bell, Seltzer, Park & Gibson, P.A.

[57] ABSTRACT

An assay for detecting the presence and amount of a hormone in culture media or a biological sample includes the steps of preincubating two antibodies specific for the hormone to be assayed in a preincubation medium that is essentially free of the hormone to be detected, contacting a sample to be tested with the preincubated antibodies, and detecting hormone-antibody complexes formed in the contacting step. This assay reduces or eliminates non-specific interference and thereby increases the sensitivity of the assay.

11 Claims, 18 Drawing Sheets

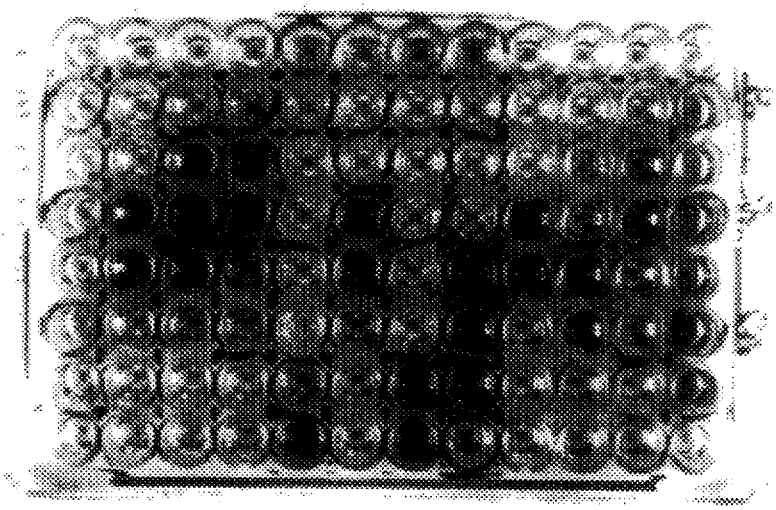
FIG. II.

METHOD FOR THE DETECTION AND/OR ASSAY OF HORMONES, AND ANTIBODIES WHICH CAN BE USED IN THE SAID DETECTION METHOD

FIELD OF THE INVENTION

The present invention relates to a method for the detection and/or assay of hormones, including the placental hormones, as well as to antibodies which can be used in the said detection method.

BACKGROUND OF THE INVENTION

The term hormones designates the substances elaborated by the various human and animal endocrine glands, and in particular the hypophysial hormones (FSH, LH, TSH, GH, ACTH, prolactin, oxytocin, MSH, ADH), the related placental hormones [human chorionic gonadotropins (hCG) and equine chorionic gonadotropins (eCG), chorionic somatomammotropin (CS), placental GH], the thyroid hormones, the adrenal hormones, the gonadal hormones and the pancreatic hormones.

Depending on their chemical structure, these hormones belong to different categories: the hormones derived from amino acids (thyroid hormones, medullo-adrenal hormones), the peptide and protein hormones (pancreatic hormones, GH, ACTH, prolactin, MSH, ADH, oxytocin), the steroid hormones (gonadal hormones, adrenocortical hormones) and the glycoprotein hormones (LH, FSH, TSH, hCG, eCG).

The glycoprotein hormones are characterised by one structural organisation: they are formed by the combination of two sub-units α and β. The α sub-unit is identical for all the glycoprotein hormones of one and the same animal species. Conversely, the β sub-unit is different from one hormone to another and confers the specificity of action. Similarly, the peptide hormones exhibit a structural relationship, as well as the polypeptide hormones (example: GH and prolactin).

These hormones are not generally secreted at constant rates, but instead exhibit variations of circulating concentration of low amplitude (micropulsatility) or, in certain cases, of great amplitude (example: peak secretion of FSH and then LH in the preovulatory phase). It is therefore necessary to have available assay methods which permit accurate and specific measurement of the circulating level of these various hormones, in the blood or in any other possible biological fluid.

These assay methods should in addition be very sensitive inasmuch as the basal concentrations of these various hormones are relatively low (for example, 0.1 ng/ml to a few ng/ml for the hypophysial hormones), except for all pathological cases.

By way of example, the detection and/or assay of the gonadotropic hormones LH and FSH is particularly important in the study of the physiology of male and female reproduction in animals and man. In mammals, for example, the functioning of the ovary comprises, during the phase of genital activity (continuous or seasonal depending on the species), a succession of ovarian cycles during which the female gametes mature at regular intervals.

The ovarian cycle comprises two phases: the follicular phase (growth of the follicle and maturation of the oocyte) leading to ovulation, the phase propitious to fertilisation, and the luteal phase (formation of the corpus luteum). FSH is responsible for the growth and the maturation of the preovulatory follicle; LH is involved more particularly in the terminal follicular growth of the latter and in the triggering of ovulation. Indeed, ovulation occurs at a very precise and regular time, for each species, after the LH peak (17 to 24 hours depending on the species). It therefore appears useful and important to be able to have at ones disposal, both in the laboratory for very precise assays as well as in the field or at home for detecting the preovulatory LH peak (in order to predict the optimum time for artificial insemination, for example), instruments for specific detection of LH, in different animals and in humans.

Similarly, the possibility of detecting very low circulating levels of chorionic gonadotropin (CG) is particularly important for the development of kits for the earliest possible diagnosis of pregnancy, especially in women.

As regards humans, a number of tests which can be carried out at home on the basis of the urine have been developed and marketed for LH and hCG.

As far as LH is concerned, a number of kits are now available which permit a precise determination of the date of ovulation. These tests use monoclonal antibodies and are based either on an agglutination reaction ("DISCRETEST", CHEFARO for ORGANON; "HI GONADO TEST", MOSHIDA) or on an immunoenzymatic reaction ("OVUSTICK", MONOCLONAL ANTIBODIES; "OVUTEST", CLONATEC; "FIRST RESPONSE"; "REVELATEST O", ARLEY-DIAGNOSTIC).

As far as hCG is concerned, several pregnancy tests are available and are based on polyclonal antibodies or, usually, monoclonal antibodies. A distinction can be made on the basis of the principle used:

haemagglutination tests (or ring tests) ("PRIMOTEST RAPIDE" from FUMOUZE; "BETA-TEST 100 UI" from SOEKAMI-LEFRANCQ; "G-TEST" from THERANOL; "ELLE-TEST BETA" from DEGLAUDE);

gold particle agglutination tests ("PREDICTOR COLOR" from NICHOLAS);

immunoenzymatic tests with indirect reading (appearance of a blue colour on a strip: "BLUE TEST" from CLONATEC) or with direct reading [appearance of a particular mark (point, bar or + sign): "BLUE POINT" from CLONATEC; "G-TEST LOGIC" from THERANOL; "PREVISION" from PHARMYGIENE];

tests combining monoclonal antibodies and migration on a membrane, without detection enzyme: "CLEAR BLUE EVIDENCE" from POLIVE-TRICOSTERIL; "PRIMOTEST MINUTE", from FUMOUZE; "G-TEST PRO" from THERANOL; "FIRST RESPONSE" from TALCO: "TEST PACK PLUS hCG" from ABBOTT). They are characterised by the appearance of a coloured mark (pink bands, blue bar, etc.).

The assay methods currently used in human medicine for these various hormones are generally, on the one hand, radioimmunological methods (for example: the "AMERLEX-M" system from AMERSHAM, the "MAI-Aclone" system from SERONO for hLH, hFSH, hTSH, hCG, etc.) and, on the other hand, enzymoimmunometric or immunometric methods (using a non-enzymatic label: latex particles, europium chelate). Among the enzymoimmunometric systems, some use a fluorescent signal (the "IMx" enzymo-microparticle system from ABBOTT; the "STRATUS SYSTEM" from AMERICAN DADE for LH, FSH, hCG etc.) or a luminescent signal (the "AMERLITE" system from AMERSHAM for LH, TSH, FSH, hCG; the "MAGIC LITE" system from CIBA CORNING for TSH, prolactin etc.). Among the immunometric systems, particular mention may be made of the "DELFIA" assay method from PHARMACIA using europium as a fluorescent label, for hLH, hFSH, hTSH, hCG, etc.

In animals, the LH assay methods are in particular:

The assay of LH in the urine of the gorilla (N. M. CZEKALA et al., J. Reprod. Fert., 1988, 82, 255–261), which uses two monoclonal antibodies, of which one is affixed on a microtitration plate and the other is bound to alkaline phosphatase. The total incubation time in this test is 4 hours (2 h: incubation of the sample on the fixed antibody; 1 h: incubation of the second bound antibody; 30 to 50 min: enzymatic detection). The sensitivity of this assay is 0.5 ng/ml.

The assay of plasmatic bovine LH (serum or culture medium) using a radioimmunological method (R. HOIER et al., Theriogenology., 1988, 30, 235–243). This assay is carried out in the presence of two antibodies ($AB_1$: anti-LH produced in the rabbit, $AB_2$: rabbit anti-IgG) and of radioactive LH (labelled with iodine-125).

This is a method involving competition, the first antibody ($AB_1$) binding to the LH of the sample or to the radioactive LH* added (incubation of 36 to 48 hours). The separation of the complex of antibody and LH from free LH* is effected using the second antibody ($AB_2$) immobilised on the walls of a tube (incubation: 3 hours, with stirring at 37° C.).

The sensitivity of this method is of the order of 1.5 ng/ml.

An ELISA assay of the LH of mice, rats, sheep and cattle, applicable to serum, tissue culture media and buffers (J. L. SPEAROW et al., Biol. Reprod., 1987, 37, 595–605), which uses the principle of competition between a LH bound to peroxidase and the LH of the sample, with respect to an antibody ($AB_1$) which is either an anti-sheep LH immune serum produced in the rabbit, or a monoclonal anti-cattle LHβ antibody, or an anti-sheep LHβ immune serum produced in the chicken.

For the antibody prepared in the rabbit, the $AB_1$-sample incubation is 16 to 24 h at 20° C. with stirring; the addition of the LH-peroxidase necessitates a fresh incubation of 16 to 24 h at 4° C. The detection is carried out using TMB (30 min to 2 h).

Under these conditions, the sensitivity of the method is 79 pg/ml.

An ELISA method for the assay of plasmatic bovine LH (W. G. ABDUL-AHAD et al., J. Reprod. Fert., 1987, 80, 1–9). This is a sandwich method on microtitration plates. The first antibody ($AB_1$) is a rabbit anti-cattle LH IgG and the second antibody ($AB_2$) is the Fab' fragment prepared from the first antibody, conjugated with the peroxidase.

They have a short protocol (4 hours) and a long protocol (20 hours). The detection threshold obtained with the short protocol is 260 pg/ml and that obtained with the long protocol is 70 pg/ml.

The detection of the peroxidase is carried out with OPD.

Another publication by the same authors (620th Meeting Dublin, Biochem. Soc. Transactions, 1985, 15, 277–278) gives details of the same assay method, using as $AB_2$ a Fab'-β lactamase conjugate.

In this article, it is specified that the duration of the assay is 4 h 30 min and that the detection threshold is 420 pg/ml.

Mention should also be made of the assay of LH in the rhesus monkey by means of an RIA, which uses labelled ovine LH and an anti-sheep LH anti-serum which reacts with the LH of numerous species.

The methods for the assay of FSH in animals are essentially of the radioimmunological type, and similarly for the other hormones.

An immunoenzymatic assay of rat prolactin has been described (A. P. SIGNORELLA et al., Anal. Biochem. 1984, 136, 372–381). This assay, of the competitive type, gives a detection threshold set at 0.6 ng/ml by applying a long protocol (24 hours).

However, in a general manner, for the assay of hormones both in humans and in animals, despite the diversity of the assay methods proposed and applied, numerous studies mention the problem of non-specific interferences in the assays, leading to erroneous results (cases of "false positives" or "false negatives") [J. P. GOSLING, Clin. Chem., 1990, 36, 1408–1427; K. A. BRENSING, Horm. Metabol. Res., 1989, 21, 697–698; P. E. GARRETT, J. Clin. Immunoassay, 1989, 12, 18–19]. This problem of non-specific interferences leads to a loss in the sensitivity and the detection threshold of the assay. Particular mention may be made of the case of an immunoenzymatic assay of hCG (B. LONGHI et al., 1986, J. Immun. Meth., 92, 89–95) for which the detection threshold was evaluated at 2.2 IU/l in a medium without serum and at 10.4 IU/l in a medium containing 20% of "hCG negative" human serum.

A number of solutions to this interference problem have been proposed, but these lead in all cases to the loss of sensitivity of the assay. These solutions in particular involve:

omitting the Fc part of the second antibody and fixing the enzyme directly on a Fab' fragment [W. G. ABDUL-AHAD et al., J. Reprod. Fert., 1987, 80, 1–9]. In this case it is necessary to apply longer times for incubation and enzymatic detection in order to compensate for the loss of sensitivity due to the treatment of the second antibody: a detection threshold of 70 pg/ml for bovine LH necessitates a protocol of 20 hours, a short protocol of 4 hours giving only a detection threshold at 260 pg/ml;

applying a test permitting measurement of the level of the non-specific signals dependent on the sample; for this purpose, the non-labelled specific antibody ($AB_1$) is substituted by another antibody similar to $AB_1$ but with an entirely different specificity (P. KASPAR et al., J. Immun. Meth., 1988, 108, 61–69). This makes it possible to determine the value of the non-specific signal, intrinsic to each sample, and to take this into consideration in the calibration of the assay, but that does not in any way eliminate this problem;

saturating the specific antibody with avidin, in the case of an ELISA of 17β-oestradiol, of competitive type using the avidin-biotin complex (D. M. BODMER and L. X. TIEFENAUER, 1990, J. Immunoassay, 11, 139–145).

Thus, all the abovementioned methods present a certain number of disadvantages:

incubation times which are long, particularly in the case of animal LH, and are not suitable for assay or for detection in the field (4 h to over 24 h);

assays which sometimes cannot be carried out on whole blood;

the absence of species-polyspecificity of these assays;

the existence of important non-specific signals, upon reading of the results, which can lead in particular to difficulties in interpreting these results;

a high detection threshold, which results therefrom, ranging from 100 pg to 1500 pg/ml in the case of animal LH, for example.

It is for this reason that the Applicant company has set itself the object of providing a process for the assay of hormones elaborated by the various endocrine glands, applicable to numerous animal species, including man, and which better satisfies the practical requirements than do the processes of the prior art, in particular:

- in that it can be carried out in less than 3 hours, in accordance with a simple protocol under conditions which can be described as rustic,
- in that it offers an unambiguous reading of the result, of the "all or nothing" type, by providing a colour in the case of the detection of a peak of acute secretion of a hormone (example: preovulatory LH peak), whereas the tests in the prior art, when they are based on a colorimetric reaction, necessitate an interpretation of the results which is very difficult for an inexperienced person (for example, the distinction between a pale or dark blue or any other colour shade, which colour shades may in addition be directly dependent on the temperature, which introduces a further error factor),
- in that it can be semi-quantitative, without the need for any reading apparatus, if a reference scale for the hormone to be assayed is provided, in addition to the samples to be tested, particularly in order to distinguish, for one and the same animal, the sample containing (for LH for example) the onset of the LH peak, the sample containing the summit of the peak (maximum value) and that containing the end of the peak (descending value); in the case of LH, such a process thus makes it possible to synchronise artificial insemination with respect to the onset of the peak or with respect to the summit of the peak, and also makes it possible to distinguish the LH secretion pulses in the male or female after an incubation of the substrate of 15 to 30 min if necessary, for a study of the micropulsatility,
- in that it presents simultaneously a species-polyspecificity and a substance-specificity,
- in that it is reproducible,
- in that it can be carried out in the field (reading by the naked eye), and
- in that it can be perfectly quantitative, substantially increasing the sensitivity of the assay and lowering the detection threshold.

SUMMARY OF THE INVENTION

The present invention relates to a process increasing the sensitivity and the specificity of the immunological detection and/or assay of human or animal hormones in culture media or in biological fluids, employing at least two identical or different antibodies specific to the hormone to be assayed, which process is characterised in that at least one of the said antibodies is pre-incubated in a medium containing plasma or serum free of the hormone (hormones) to be detected and/or to be assayed.

Pre-incubated antibody is understood, within the meaning of the present invention, as an antibody which is "attenuated"—by being brought into contact with or passed through an appropriate chromatography column—by any substance capable of inducing a non-hormonal and non-specific serum interference.

According to the invention, the biological fluid is advantageously serum, plasma, whole blood, milk or urine.

In the continuation of the present application, the medium containing serum or plasma, free of the hormone to be detected and/or to be assayed, is called INC medium.

According to an advantageous mode of implementation of this process, the said INC medium comprises a serum or a plasma from an animal having undergone ablation of an endocrine gland, suitable for the assay, and is optionally combined with an appropriate buffer.

According to an advantageous arrangement of this mode of implementation, the INC medium is free of hypophysial hormones and advantageously comprises a serum or a plasma from a suitable hypophysectomised animal, optionally combined with a suitable buffer.

As suitable buffer, mention may be made in particular of a buffer with a neutral pH combined with a surfactant agent, and in particular a PBS-Tween-BSA buffer.

According to an advantageous form of this arrangement, the INC medium comprises a serum or a plasma from a hypophysectomised ram, combined with a suitable buffer.

According to another advantageous arrangement of this mode of implementation, the plasma or serum from an animal having undergone ablation of a suitable endocrine gland and the suitable buffer are in a ratio of 1:1.

According to the invention, the said process is advantageously a highly specific and sensitive enzymoimmunometric test for the detection of at least one hormone.

According to an advantageous mode of implementation of the said enzymoimmunometric test, the first antibody is fixed on a suitable solid support and the second antibody pre-incubated in a medium containing a plasma or a serum free of the hormone to be detected and/or to be assayed (INC medium), and optionally linked to a suitable enzyme, are brought into contact with the biological fluid to be tested, after which the enzymatic activity associated with the solid and/or free phase is detected by any suitable means.

According to an advantageous arrangement of this mode of implementation, when the second antibody preincubated in the said INC medium is not linked to an enzyme, the reaction is then detected by the introduction of a third antibody linked to a suitable enzyme, preincubated in the said INC medium and binding specifically to the second antibody.

According to another advantageous arrangement of this mode of implementation, the said INC medium is free of hypophysial hormones.

According to this latter arrangement, the first and second antibodies are advantageously chosen from the group which comprises the monoclonal anti-FSH, anti-LH, anti-TSH, anti-GH, anti-ACTH, anti-prolactin, anti-oxytocin, anti-ADH, anti-MSH, anti-hCG and anti-eCG antibodies and the polyclonal anti-FSH, anti-LH, anti-TSH, anti-GH, anti-ACTH, anti-prolactin, anti-oxytocin, anti-ADH, anti-MSH, anti-hCG and anti-eCG antibodies.

According to an advantageous form of this arrangement, the polyclonal anti-LH antibodies are obtained in particular by immunising a suitable animal with a mixture of different isoforms of ovine LH, then by appropriate purification of the immune serum obtained, which polyclonal antibodies have a percentage of cross-reactions with the other glycoprotein hormones, such as FSH, of less than 4%, that is to say a specificity with respect to LH, in that they have a polyspecificity of recognition of the LH of numerous animal species and, in particular, at least the ovine, bovine, caprine, porcine, canine, cameline and murine species, as well as the cervidae, and in that they have an affinity with respect to ovine LH of the order of $10^9 M^{-1}$, respectively in two different animal species.

According to this advantageous form, the first and second antibodies are advantageously chosen from the group which comprises polyclonal rabbit anti-sheep LH antibodies and polyclonal horse anti-sheep LH antibodies, and the third antibody is advantageously chosen from the group which comprises the horse anti-IgG and the rabbit anti-IgG linked to a suitable enzyme.

Likewise in accordance with this advantageous form, the first antibody is a polyclonal rabbit anti-sheep LH antibody, the second antibody is a polyclonal horse anti-sheep LH antibody, and the third antibody is a horse anti-IgG linked to a suitable enzyme and in particular to a peroxidase or to a β-galactosidase.

Likewise in accordance with this advantageous form, the mixture of different isoforms of ovine LH employed for the immunisation advantageously contains at least two isoforms of ovine LH.

The different isoforms of ovine LH are preferably in equimolar quantities.

An appropriate purification of the said polyclonal anti-LH antibodies can be carried out, depending on the case, either by affinity chromatography or by ion-exchange chromatography.

According to another mode of implementation of the said enzymoimmunometric test, prior to the introduction of the second antibody, the solid support is saturated with INC medium.

Indeed, in an unexpected manner, the preincubation with the INC medium, as defined hereinabove, makes it possible:
- to eliminate the problems of non-specific signals customarily found in this type of assay, by neutralising any non-specific serum interference which can lead to a decrease in the sensitivity of an assay,
- to increase considerably, for this reason, the sensitivity of this type of assay, which is particularly important in the case of hormones with a low circulating level,
- thus, to assay all the hormones, and in particular the suitable hypophysial and placental hormones, obtaining results which can be interpreted correctly and easily.

Consequently, the immunological assay and, more particularly, the enzymoimmunometric assay of the hormones, in accordance with the invention, presents at one and the same time the characteristics of a quantitative assay, by affording a very good sensitivity and a very good reproducibility, and of a qualitative assay on account of its ease of implementation and interpretation.

The efficacy and the advantages of the process according to the invention described hereinabove are illustrated in particular by the enzymoimmunometric assay of luteinising hormone (LH). Indeed, this assay presents at one and the same time the characteristics of a quantitative assay, by affording a very good sensitivity (detection threshold: 60 pg/ml) and a very good reproducibility, and of a qualitative assay on account of its ease of implementation and interpretation. It can therefore be used both in the laboratory for very accurate assays (example: measurement of the micropulsatility of the secretion of LH) and in the field (detection of the preovulatory LH peak for artificial insemination of synchronised females and/or of superovulated females, offering embryos).

This assay of LH, which can be used in numerous species (bovine, ovine, caprine, porcine, cameline, canine, murine and cervidae), permits the accurate detection of the preovulatory LH peak in the female and is of an obvious physiological and agronomic interest. It will in addition permit a good calculation of the optimum time chosen for the artificial insemination in each species in question. Indeed, the interval between the LH peak and ovulation is constant in each species; in contrast, the interval of time separating the onset of heat (indicator used hitherto) and the LH peak fluctuates greatly between the individuals of one and the same breed.

The test according to the invention therefore proves to be an indispensable tool for controlling this variability factor important for the success of fertilisation of the oocytes and collection of good-quality embryos. Indeed, knowing the precise time of ovulation, by virtue of the detection of the LH peak, and of the artificial insemination, it is possible to deduce therefrom at what stage of development the embryos will be which it is desired to collect. This point is important insofar as embryos which are too immature or too advanced are not marketable (example: broken pellucid membrane).

Finally, this test for the assay of animal LH is of interest in the context of the development of a new treatment (synchronisation, superovulation) or the extension of these treatments to a breed, or even a species, whose preovulatory physiology is poorly understood (example: cervidae).

Similarly, the enzymoimmunometric assay of human LH, carried out using the process according to the invention, presents at one and the same time the characteristics of a quantitative assay, on account of the very good sensitivity acquired by virtue of the said process, and of a qualitative assay on account of the ease of implementation and interpretation acquired likewise by virtue of the process according to the invention. It can therefore be used in the laboratory or at home for individual use ("home test"); in this latter case, it will serve as a kit for detection of the preovulatory LH peak, characterised by the appearance of an unambiguous green colour, making it possible to predict the time of ovulation in women.

Moreover, when it is desired to carry out an assay having species-polyspecificity, the antibodies must have particular qualities; in this case, the choice of the antibodies is important for suitable implementation of the process according to the invention. It is for this purpose that the Applicant company has also developed antibodies particularly adapted to the process according to the invention.

The present invention also relates to polyclonal anti-LH antibodies, characterised in that they are obtained by immunising a suitable animal with a mixture of different isoforms of ovine LH, then by appropriate purification of the immune serum obtained, in that the said polyclonal antibodies have a percentage of cross-reactions with the other glycoprotein hormones, such as FSH, of less than 4%, that is to say a specificity with respect to LH, in that they have a polyspecificity of recognition of the LH of numerous animal species and, in particular, at least the ovine, bovine, caprine, porcine, canine, cameline and murine species, as well as the cervidae, and in that they have an affinity with respect to ovine LH of the order of $10^9 M^{-1}$.

According to an advantageous embodiment of the said antibodies, the suitable animal is the rabbit; polyclonal anti-sheep LH antibodies are thus obtained from the rabbit.

According to another advantageous embodiment of the said antibodies, the suitable animal is the horse; polyclonal anti-sheep LH antibodies are thus obtained from the horse.

According to another advantageous embodiment of the said antibodies, the mixture of different isoforms of ovine LH employed for the immunisation advantageously contains at least two isoforms of ovine LH.

According to an advantageous feature of this latter embodiment, the different isoforms of ovine LH are in equimolar quantities.

An appropriate purification of the said polyclonal anti-LH antibodies can be effected, depending on the case, either by affinity chromatography or by ion-exchange chromatography.

The present invention moreover relates to a reagent for the implementation of the process for the immunological detection and/or assay of hormones in animals, including man, according to the invention, characterised in that it comprises an anti-hormone antibody capable of being used as the first, second and/or third antibody in the said process, which antibody is pre-incubated in an INC medium.

The present invention moreover relates to a kit for the detection and/or diagnosis of hormones, such as the hypophysial hormones (FSH, LH, TSH, GH, ACTH, prolactin, oxytocin, ADH, MSH), the thyroid hormones, the adrenal hormones, the genital hormones and the pancreatic hormones in man or animal, hCG and eCG, or a kit for the implementation of the test according to the invention, characterised in that it comprises, in addition to useful quantities of suitable buffers for the implementation of the said detection:

suitable amounts of an antibody chosen from among the appropriate anti-hormone antibodies, including the anti-LH antibodies and the reagents according to the invention;

suitable amounts of conjugates of suitable enzyme and antibody, which antibody is chosen from the group which comprises the appropriate anti-hormone antibodies, including the anti-LH antibodies and the reagents according to the invention, or from the group which comprises the appropriate anti-IgG, which conjugates are pre-incubated in an INC medium, in conformity with the reagent described hereinabove;

suitable quantities or amounts of a substrate for detection of the enzyme;

a suitable solid support, if necessary; and suitable quantities or amounts of an INC medium.

According to an advantageous embodiment of the said kit, when it is used for the assay of LH, it comprises:

suitable amounts of a polyclonal antibody chosen from among the polyclonal rabbit anti-sheep LH antibodies, the polyclonal horse anti-sheep LH antibodies according to the invention and the reagents according to the invention containing one of the abovementioned polyclonal anti-sheep LH antibodies;

suitable amounts of conjugates of suitable enzyme and antibody, which antibody is chosen from the group which comprises the polyclonal rabbit anti-sheep LH antibodies, the polyclonal horse anti-sheep LH antibodies according to the invention or from the group which comprises the horse anti-IgG and the rabbit anti-IgG, which conjugates are pre-incubated in an INC medium, in conformity with the reagent described hereinabove;

suitable quantities or amounts of a substrate for detection of the enzyme;

a suitable solid support, if necessary;

a sampling capillary tube; and optionally, suitable quantities or amounts of an INC medium.

According to another advantageous embodiment of this kit, the enzyme is chosen from the group which comprises the peroxidases and β-galactosidase.

The substrates for detection of the peroxidase are advantageously OPD and ABTS; the substrate for detection of β-galactosidase is advantageously 4-methyl-umbelliferyl-β-D-galactopyranoside (MUG) and ortho-nitropheny-β-O-galactopyranoside (ONPG).

The solid support is advantageously chosen from the known supports, such as microtitration plates, sticks, strips, balls or membranes.

According to another advantageous embodiment of this kit, it comprises:

a series of appropriate solid supports covered with an antibody chosen from among the appropriate anti-hormone antibodies, including the anti-LH antibodies and the reagents according to the invention, which solid supports are optionally saturated with INC medium;

suitable amounts of an antibody chosen from the group which comprises the antibodies anti-FSH, anti-LH, including the anti-LH antibodies according to the invention, anti-TSH, anti-GH, anti-ACTH, anti-prolactin, anti-oxytocin, anti-ADH, anti-hCG, anti-eCG and anti-PMSG, different from the first antibody and the reagents according to the invention;

suitable amounts of appropriate peroxidase/anti-IgG conjugates, pre-incubated in an INC medium, in conformity with the reagent described hereinabove; and suitable quantities of a substrate for detection of the peroxidase.

According to an advantageous feature of this embodiment, it comprises:

a series of appropriate solid supports covered with an antibody chosen from the group which comprises the polyclonal rabbit anti-sheep LH antibodies according to the invention and the reagents according to the invention containing the abovementioned polyclonal rabbit antibody, which solid supports are optionally saturated with INC medium;

suitable amounts of an antibody chosen from the group which comprises the polyclonal horse anti-sheep LH antibodies and the reagents according to the invention containing the abovementioned polyclonal horse antibody;

suitable amounts of conjugates of peroxidase and horse anti-IgG, pre-incubated in an INC medium, in conformity with the reagent described hereinabove;

suitable quantities of a substrate for detection of the peroxidase; and a sampling capillary tube.

According to an advantageous feature of this embodiment, it comprises:

a series of appropriate solid supports covered with an antibody chosen from the group which comprises the polyclonal rabbit anti-sheep LH antibodies according to the invention and the reagents according to the invention containing the abovementioned polyclonal rabbit antibody, which solid supports are optionally saturated with INC medium;

suitable amounts of conjugates of β-galactosidase and polyclonal horse anti-sheep LH antibodies, pre-incubated in an INC medium, in conformity with the reagent described hereinabove;

suitable quantities of a substrate for detection of β-galactosidase; and a sampling capillary tube.

In addition to the preceding features, the invention furthermore comprises other features which will emerge from the description which follows.

BRIEF DESCRIPTION OF THE FIGURES

FIG. 11 is a photo of a plate used in an ELISA procedure to detect pre-ovulatory peaks in superovulated goats.

DETAILED DESCRIPTION

Figure 1:
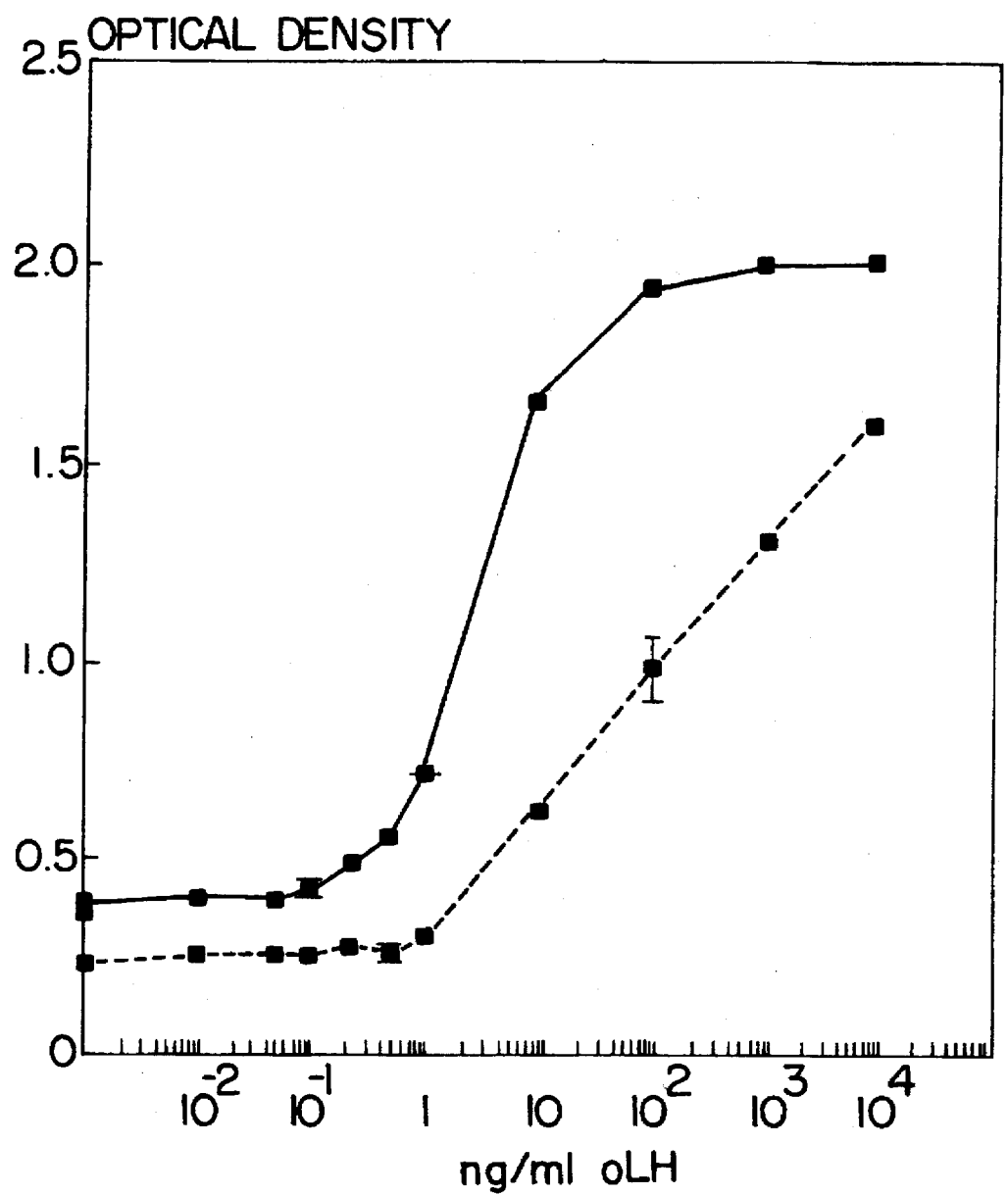
FIG. 1 is a graph of color reaction as a function of ovine LH concentration indicative of enzymatic activity.

The invention will be better understood with the aid of the remainder of the description which follows, and in which reference is made to exemplary embodiments of the polyclonal antibodies according to the invention and to exemplary implementations of the test according to the invention.

It should be clearly understood, however, that these examples and drawings are given solely by way of illustration of the object of the invention, and that they do not in any way constitute a limitation thereof.

EXAMPLE 1

Preparation of the polyclonal anti-animal LH antibodies according to the invention.

1) Characteristic of the immunogen:

The antigen used for the immunisations is an equimolar mixture of various purified fractions of ovine LH (oLH). These fractions have been listed thus:

| oLH | 1051 | 1083 |
|-----|------|------|
|     | 1055 | 1085 |
|     | 1072 | 1086 |

2) Process for obtaining polyclonal anti-LH antibodies:

a.2) Antibody produced in the horse (pony $MW_5$)

Each injection contains 1 mg of the above-mentioned oLH mixture, dissolved in 2.5 ml of sterile physiological serum and prepared as an emulsion in 2.5 ml of Freund's complete adjuvant.

The immunisation protocol consists of 6 injections followed by 8 boosters, after each of which a bleeding was carried out, 2 weeks later. The exact sequence of the injections is illustrated in Diagram I below:

Diagram I

| Injections | boosters | | | | | | | |
|---|---|---|---|---|---|---|---|---|
| 1 2 3 4 5 6 | $B_1$ | $B_2$ | $B_3$ | $B_4$ | $B_5$ | $B_6$ | $B_7$ | $B_8$ |
| Every 2 weeks | 1 month ½ | 2 months | 3 months | 2 months | 5 months | 7 months | 2 months | 1 month |
| No bleeding | One bleeding 2 weeks after each booster | | | | | | | | b.2) Antibody produced in the rabbit:

Each injection contains 0.1 mg of the oLH mixture, dissolved in 0.5 ml of sterile physiological serum. An emulsion of all this is prepared in 0.5 ml of Freund's complete adjuvant and is injected at multiple points along the vertebral column (intradermal injections).

The immunisation protocol consisted of 4 injections carried out every two weeks. Then, there followed a series of 12 boosters carried out in accordance with the sequence illustrated below in Diagram II:

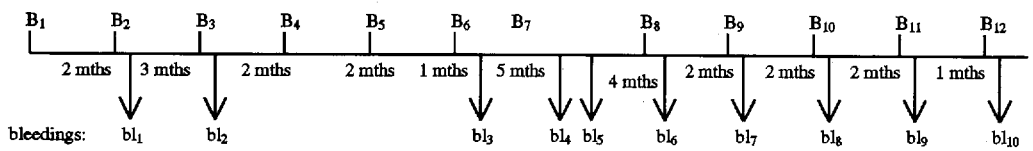

Diagram II

The bleedings are carried out two weeks after the indicated boosters, with the exception of $bl_5$ which was carried out four weeks after $B_7$.

Three rabbits were immunised: two received the 12 boosters, and one received only 6 boosters.

3) Processes for purification of the polyclonal anti-LH antibodies:

a.3) Purification of the horse immune serum:

This purification is carried out by ion-exchange chromatography on DEAE-Trisacryl (IBF-FRANCE) on a K26/40 column from PHARMACIA.

The immune serum (15 ml) is dialysed for one night against a 0.025M Tris-HCl, 0.035M NaCl buffer, pH 8.8 at 4° C. The column is equilibrated in parallel with this same buffer. After filtration of the dialysed serum, the latter is passed over the column at a rate of 50 ml/hour. The eluted fraction obtained at the column outlet contains the IgG of the serum and represents the antibody-enriched fraction which is used in the assay. Before use, this fraction is dialysed against PBS pH 7.4 (0.01M $KH_2PO_4/K_2HPO_4$, 0.15M NaCl). It is then concentrated by ultrafiltration on a MINI-CON support (AMICON, Ireland) until a concentration of between 5 and 10 ng/ml is obtained. It is stored in aliquot form at −20° C., diluted in 50% of bi-distilled glycerol.

b.3) Purification of the rabbit immune serum:

The purification is carried out by affinity chromatography on protein A. The gel Protein A-Sepharose CL-4B (PHARMACIA) is used and is poured into a 2×10 cm column (PHARMACIA). The serum (5 ml) is first dialysed against 0.1M phosphate buffer, pH 8, filtered and passed over the column equilibrated with the same buffer (rate: 15 ml/h).

The immunoglobulins are desorbed using a pH gradient from 6 to 4.5 and prepared with a 0.1M citrate/citric acid buffer, then with a pH 3 buffer (0.1N acetic acid, 0.15M NaCl).

The eluted fractions are neutralised with 1M phosphate buffer, pH 8, and dialysed against PBS before being concentrated by ultrafiltration (cf. hereinabove) and stored at −20° C. in 50% of bi-distilled glycerol.

The experimental protocols used in 3 a) and b) were carried out in accordance with the instructions provided by the suppliers and completed with "Techniques Immunoenzymatiques" ["Immunoenzymatic Techniques"] Th. TERNYNCK and S. AVRAMEAS, INSERM Publications, 1987.

In all cases, the exact concentration of the purified fractions is evaluated by measuring the optical density at 280 nm, on the basis that an o.d. of 1.4 corresponds approximately to a solution of IgG at 1 mg/ml.

4) Characteristics and specificity of the anti-LH antibodies according to the invention:

Cross-reactions:

Given the structural similarity with other glycoprotein hormones, it is essential, for the purpose of obtaining a reliable assay, to have antibodies which recognise only LH and do not present any cross-reaction with FSH and TSH in the animal species studied. Consequently, various FSH and TSH were tested in the assay in order to evaluate the percentage of cross-reaction with these.

In the same way, LH of various animal species were tested in the assay and their percentage cross-reaction was calculated.

The percentage cross-reaction is calculated in a conventional way by comparing the dose-response curves obtained, on the one hand, with a range of concentrations of each LH tested and, on the other hand, with a range of concentrations of ovine LH. From the "reference" curve obtained with the ovine LH, let Y be the concentration giving 50% of the maximum optical signal ($ED_{50}$). From the curve obtained with another LH, let X be the concentration corresponding to the same optical density as that used to define Y:

The percentage cross-reaction is equal to X/Y×100 a) Cross-reactions obtained with the various LH tested:

| Source of the LH | Bovine | Caprine | Porcine | Canine | Cameline | Murine (rat) |
|---|---|---|---|---|---|---|
| Percentage cross-reaction | 97% | 45.5% | 34% | 20% | 55.6% | 20% | b) Cross-reactions obtained with the FSH and TSH of the animal species for which the LH is recognised by the two antibodies (AB1 and AB2) specific to the assay:

| Animal species | Ovine | Bovine | Porcine | Murine (rat) |
|---|---|---|---|---|
| FSH | 0.05% | 3.12% | 0.06% | 0.03% |
| TSH | 8% | 2% | 0.62% | 1.15% |

It should be noted that the percentage cross-reaction with ovine TSH is high (8%) and is perhaps due to a high degree of contamination in the hormonal preparation used.

Affinity of the anti-LH antibodies (rabbit and horse antibodies) used in the assay:

The affinity constant (Ka) was measured in accordance with the method described by B. FRIGUET et al. ((1985), J. Immunol. Methods, vol. 77, 305–319) and is calculated using the KLOTZ representation:

rabbit anti-sheep LH antibody, $Ka=1.87.10^9 M^{-1}$ horse anti-sheep LH antibody, $Ka=2.10^9 M^{-1}$.

EXAMPLE 2

Immunoenzymometric test according to the invention: assay of animal LH.

A—Assay principle:

The method used is ELISA (enzyme-linked immunosorbent assay), that is to say all the reagents are bound to a solid phase. The solid phase used is, in a non-limiting manner, a microtitration plate with 96 wells made of Luxlon (hydrophobic plastic), but the assay can be carried out on other types of plates or other types of supports, in particular sticks, strips, balls or membranes.

The assay according to the invention, of the "sandwich" type, uses two polyclonal antibodies as defined hereinabove, that is to say prepared from one and the same antigen, ovine LH, but produced in two different animal species (the rabbit and the pony);

the first antibody (AB1) is fixed on the bottom of the wells of a microtitration plate. This first antibody was produced in a rabbit;

after washing the plate, the plate is optionally saturated with a suitable medium to which is added serum or plasma free of LH. This medium is hereinafter called INC medium;

the sample to be assayed is incubated; a volume of 10 µl per well is necessary, that is to say the assay can be carried out on the basis of one drop of plasma or of blood. The assay on the basis of blood is carried out in a modified medium containing heparin, hereinafter called S medium;

washing of the plate, incubation of the second antibody previously diluted in the INC medium. This second antibody was produced in a pony;

washing of the plate, incubation of a third antibody linked to an enzyme (goat antibody—horse anti-IgG linked to peroxidase or β-galactosidase). Before it is deposited, the antibody is first diluted in the INC medium;

after washing, the enzymatic activity associated with the solid phase is detected using a chromogenic or fluorogenic substrate specific to the enzyme used. The intensity of the colour reaction or of the fluorescent signal obtained is proportional to the concentration of the LH contained in the assayed sample, as is shown by the curves in FIG. 1. The reaction time necessary is 5 minutes for detection of the preovulatory peak and 15 minutes for a precise quantitative measurement of low circulating levels.

The role of the order of use of the two specific antibodies was determined by comparing the two possible combinations:

curve (-■-): AB1 rabbit AB2 horse and curve (--■--): AB1 horse AB2 rabbit.

The results shown in FIG. 1 were obtained on a range of dilutions of ovine LH effected in phosphate buffer (standard range). As can be seen very clearly, the AB1 rabbit/AB2 horse combination (-■-) gives better results both from the point of view of the detection threshold and the sensitivity of the assay.

Figure 2:
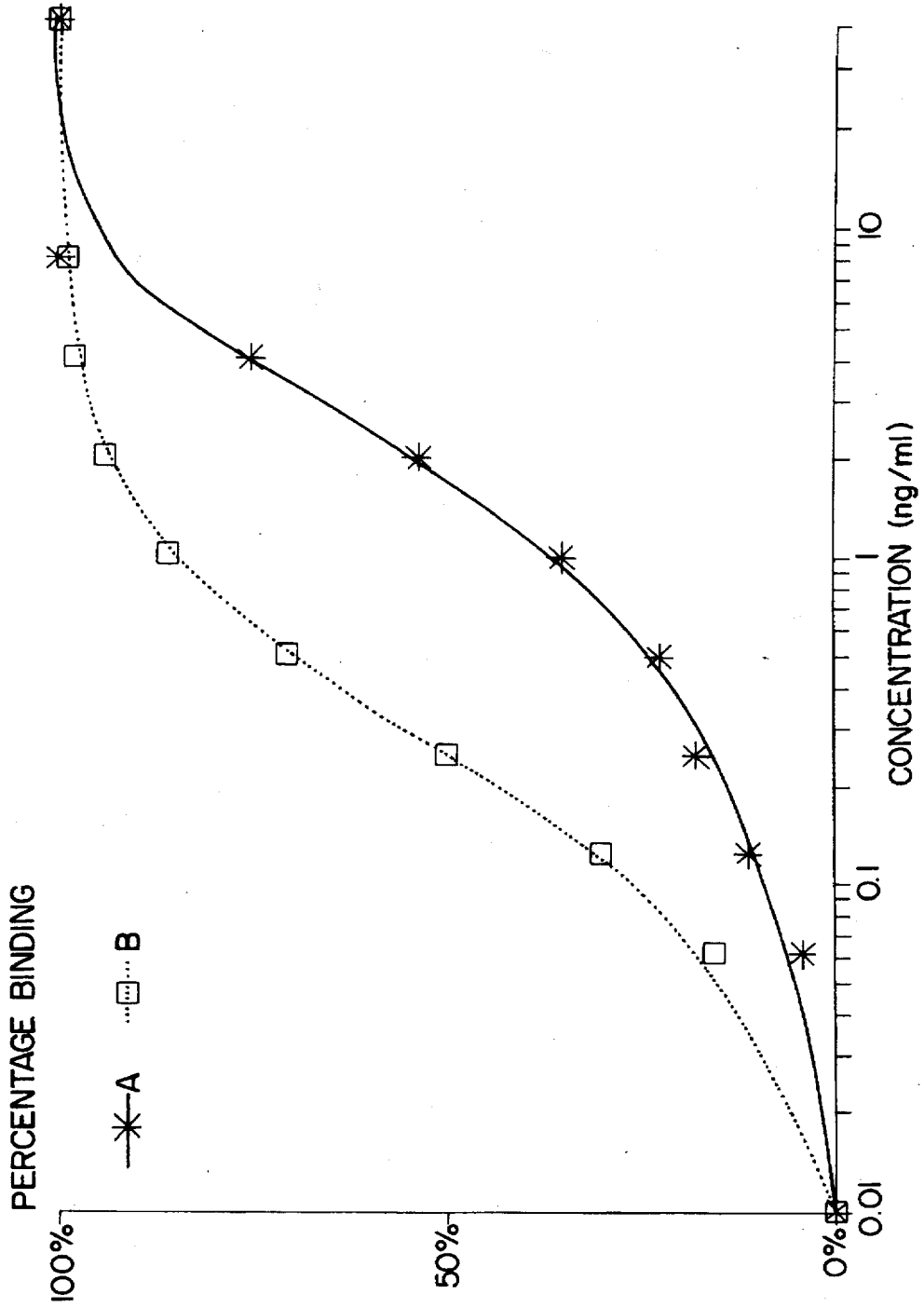
FIG. 2 is a graph of percent binding as a function of oLH concentration which indicates that the sensitivity of the assay decreases when two antibodies produced in the same species are used.

The fact that two antibodies produced in two different animal species were used is crucial for obtaining the improved sensitivity of the test according to the invention, compared to the tests in the prior art. This particular selection of polyclonal antibodies offers more probability of the LH molecule being recognised via different epitopes by each of the immune serums compared to immune serums produced in the same species. FIG. 2 shows the decrease in the sensitivity of the assay when use is made of two antibodies (AB1 and AB2) produced in the same species (horse, for example: AB1=horse AB at 10 µg/ml, and AB2=horse AB/β-galactosidase at 5 µg/ml).

The use of one and the same antibody as AB1 and as $AB_2$ (curve -*-) results in a considerable loss in the sensitivity of the assay, as can be seen from the curves in FIG. 2. For the oLH concentration giving 50% binding, a sensitivity of 250 pg/ml is observed in the case of a protocol according to the invention (AB1 rabbit, AB2 horse, AB3 anti-horse-peroxidase; curve (..□..) against 1.8 ng/ml in the case of a protocol with two identical antibodies (curve -*-) as specified hereinabove. This latter figure corresponds to a residual efficacy of 15%, with respect to the assay carried out under the optimum conditions (according to the invention, see in particular Example 3 hereinbelow). The percentage binding was calculated in accordance with the formula B-NS/T in which B is the optical density measured for each point in the range, NS is the optical density measured for the zero point of the range, and T represents the optical density measured for the highest point in the range.

B—Characteristics of the incubation media according to the invention:

b 1) Blood dilution medium:

In the case of an assay carried out directly from blood, the medium for dilution of the sample must have heparin added to it in order to prevent coagulation. The blood is then recovered in PBS-Tween-BSA with addition of 0.2% heparin, i.e. 100 µl of heparin per 50 ml of PBS-Tween-BSA (see Example 3).

2) INC medium:

2.a) Composition of the INC medium:

This medium is composed of at least 50% of serum or plasma taken from a hypophysectomised ram and diluted in PBS-Tween-BSA.

2.b) Obtaining the serum from a hypophysectomised ram:

The animal is fasted for 48 hours prior to the operation. The latter is performed under anaesthesia; the hypophysis is ablated via the floor of the mouth.

Blood samples are taken every day in order to monitor the drop in level of circulating LH following the hypophysectomy. When this is no longer detectable, the animal is anaesthetised and bled white. The blood is collected using heparin in order to recover the plasma or is coagulated in order to separate the serum therefrom. Plasma and serum are kept at $-20°$ C.

The animal is bled between 5 and 7 days following the hypophysectomy.

Figure 3:
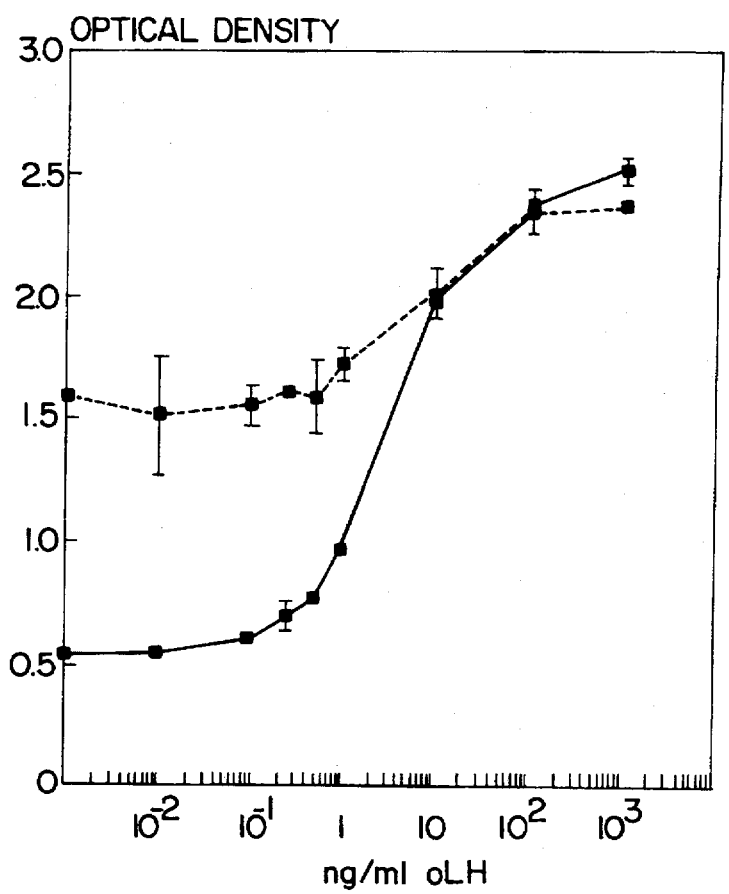
FIG. 3 is a graph of optical density as a function of LH concentration which indicates that the inclusion of INC medium in the assay improves assay performance.

2.c) Role of the INC medium in the assay:

It is essential, in a plasmatic assay, to prepare the reference scale in a dilution medium containing the same proportion of plasma as the sample preparations to be assayed. If these are diluted ten-fold, the reference scale will be prepared with serum from a hypophysectomised animal (LH$^-$) diluted ten-fold in normal dilution buffer (PBS-BSA-Tween). FIG. 3 shows the results obtained with a reference scale prepared in dilution buffer (-■-) and those obtained with a scale prepared in this same buffer with the addition of 10% of hypophysectomised animal serum (--■--) (assay of type AB3-peroxidase/OPD, see Example 3). A particularly troublesome interference of the serum LH$^-$ is observed in the assay, especially in the zone of low concentrations of ovine LH (oLH), which conceals all the real sensitivity of the assay.

Consequently, the two anti-LH immune serums were attenuated on sheep IgG in order to eliminate any interference between IgG originating from different animal species (ovine on the one hand, and lapine and equine on the other hand). The results obtained showed only a slight decrease in the considerable non-specific signal, observed without prior attenuation.

It would appear that another source of interference can arise, for example due to a substance immunologically close to LH and recognised as such.

Similar results were described in a radioimmunological assay of LH in rhesus monkeys (NEILL et al., 1977, PECKHAM et al., 1977). Using ovine LH as iodinated tracer and an anti-sheep LH antibody, the authors observed a very considerable non-specific interference for the low concentrations of the range; on the other hand, they observed no interference when using the iodinated monkey LH and an anti-monkey LH antibody. This "LH-like" was not purified, and its interfering effect was not avoided by the authors.

The process according to the invention has, for its part, the advantage of making it possible to overcome this difficulty, by virtue of the INC medium which has permitted the development of a very sensitive, reliable and rapid assay.

C—Substrates and enzymatic conjugates:

This assay is not dependent on the enzyme used as label. Two enzymes have been used hitherto, peroxidase and β-galactosidase, the first with two chromogenic substrates, the second with a fluorogenic substrate.

1) Substrates used:

* for peroxidase:

OPD (ortho-phenylenediamine)

ABTS (2-2'-azinobis(3-ethylbenzthiazoline-6-sulphonic acid).

The OPD is prepared at the time of use, at 0.5 mg/ml in acetate buffer (0.1M sodium acetate) pH 5.6, with addition of 0.2% hydrogen peroxide.

The optical density is measured at 492 nm; the reaction is demonstrated by the appearance of an orange to brown colouring and is stopped with 50 µl of 2N sulphuric acid.

The ABTS is prepared in 0.05M citrate buffer, pH 4: for 12 ml of citrate buffer, there are added 60 µl of stock ABTS and 50 µl of 2% hydrogen peroxide, the measurement of the optical density being carried out at 405 nm.

Under the action of the peroxidase, the colourless ABTS becomes green.

Citrate buffer: 2 volumes of citric acid ((5.3 g/l) $C_6H_8O_7$, 1 $H_2O$)+one volume of sodium phosphate ($Na_2HPO_4$, 12 $H_2O$) (17.73 g/l). The reaction can be stopped with 20 µl of 10% SDS, this having no obligatory character.

* For β-galactosidase:

4-Methylumbelliferyl-β-D-galactopyranoside (MUG), commercial product (SIGMA M 1633):

2.5 mg are dissolved in 12.5 ml of 0.1M phosphate buffer, pH 7.4 (see composition in Example 3). The reaction is stopped with 50 µl of 2M sodium carbonate.

The fluorescence signal is read using a spectral fluorimeter for ELISA plates.

The excitation wavelength=360 nm, the emission wavelength=448 nm.

2) Enzymatic conjugates:

* The antibody conjugated with peroxidase (AB3: horse anti-IgG antibody coupled to peroxidase) is available commercially: Jackson Immunoresearch Laboratories Inc., code No. 108-035-003.

* The antibody conjugated with β-galactosidase was made in two ways:

either the horse anti-LH antibody is coupled directly to the β-galactosidase (AB2-β-galactosidase), or a horse anti-IgG antibody is coupled to the β-galactosidase (AB3-β-galactosidase).

* Carrying out the coupling:

This was performed in accordance with the process of coupling to glutaraldehyde in two stages (Techniques Immunoenzymatiques [Immunoenzymatic Techniques], Th. TERNYNCK and S. AVRAMEAS, INSERM Publications, 1987, pages 33–34).

The horse anti-LH antibody is purified by ion-exchange chromatography (DEAE), as is the horse anti-IgG antibody (produced in the sheep).

D—Buffers:

* 0.1M carbonate buffer, pH 9.6: dilute 10-fold a molar solution of carbonate/sodium bicarbonate in distilled water.

* PBS: dilute 100-fold a molar solution of mono- and bi-potassium phosphate, pH 7.4, in a 0.15M solution of NACl.

* PBS-Tween: add 0.1% (1 ml in 1 liter) of Tween 20 in PBS.

* PBS-Tween-BSA: add 0.2% of BSA in PBS-Tween.

EXAMPLE 3

Quantitative colorimetric assay with the AB3-peroxidase system: assay of animal LH.

1.a) AB3-peroxidase/ABTS substrate system:

* Sensitisation of plates or coating:

100 µl of the rabbit anti-sheep LH antibody (AB1) prepared in 0.1M carbonate buffer, pH 9.6, at a concentration of 7.5 µg/ml are distributed into the wells. The plate is incubated for 1 hour at 37° C., and then for one night at 4° C. The plate is then washed with PBS-Tween 5 times at the rate of 300 µl per well, either manually or using an automatic washer for ELISA plates.

The AB1 can be prepared at a different concentration: 10 µg/ml or 5 µg/ml; the extreme concentrations being 20 µg/ml and 2.5 µg/ml.

* Coating or saturation of the wells:

After washing, the wells are filled with 100 µl of INC medium and the plate is incubated for 30 minutes at 37° C. At this stage, the plate is either used for the continuation of the assay or is emptied, dried at 37° C. and then kept in a dry atmosphere, sealed under plastic.

* Incubation of the samples and of the range:

The oLH range (ovine LH) is prepared in PBS-Tween-BSA containing serum from a hypophysectomised animal and diluted to 1/10th. It comprises the following concentrations: 60 pg/ml, 125 pg/ml, 250 pg/ml, 500 pg/ml, 1 ng/ml, 2 ng/ml, 4 ng/ml, 8 ng/ml and, optionally, 40 ng/ml of oLH. It is double-deposited, 100 µl per well.

The plasmas to be assayed are diluted 10-fold in PBS-Tween-BSA. They are double-deposited or triple-deposited, with 100 µl per well. (The dilution of 1/10th is not obligatory and may be greater or less, if necessary). The whole system is incubated for 1 hour at 37° C. After this, the plate is washed 5 times with PBS-Tween (300 µl/well) in the same way as above.

* Incubation of the second anti-LH antibody (horse):

This antibody, AB2, is prepared beforehand in INC medium: it is diluted to a concentration of 5 µg/ml in the INC medium and is incubated for 30 minutes at 37° C. before being deposited in the wells, 100 µl per well.

Once the AB2 is distributed, the plate is incubated for 1 hour at 37° C. As in the case of rabbit AB1, the concentration of 5 µg/ml for AB2 is not obligatory, but it must in all cases be less than that of AB1. It can be between 15 µg/ml (if AB1 is at 20 µg/ml) to 2.5 µg/ml, or even 1 µg/ml (if AB1 is at 2.5 µg/ml). After the incubation, the plate is washed 5 times in the same way as above with PBS-Tween.

* Incubation of the third horse anti-IgG antibody linked to peroxidase:

AB3 is also pre-incubated for 30 min at 37° C. in the INC medium at a dilution of 1/5000th (depending on the manufacturer's instructions) before being deposited in the wells (100 µl per well). Incubation is carried out for 1 hour at 37° C. The plate is then washed 5 times with PBS-Tween.

* Depositing the substrate of peroxidase:

100 μl of ABTS prepared as described hereinabove (C) are deposited; after 5 minutes, the wells corresponding to a high concentration of oLH are coloured green.

After 15 minutes of incubation at 37° C., a first measurement of the optical density is carried out in order to provide a first indication of development of the reaction. After this, the plate is again incubated for 15 minutes at 37° C., if the reaction has to be continued, particularly in the case of samples with a low LH content. Then, a definitive reading of the results is carried out. The enzymatic reaction can be stopped by adding 20 μl of 10% SDS per well.

The reading of the optical density is carried out using an automatic spectrophotometer for ELISA plates, equipped with a 405 nm filter.

Figure 4:
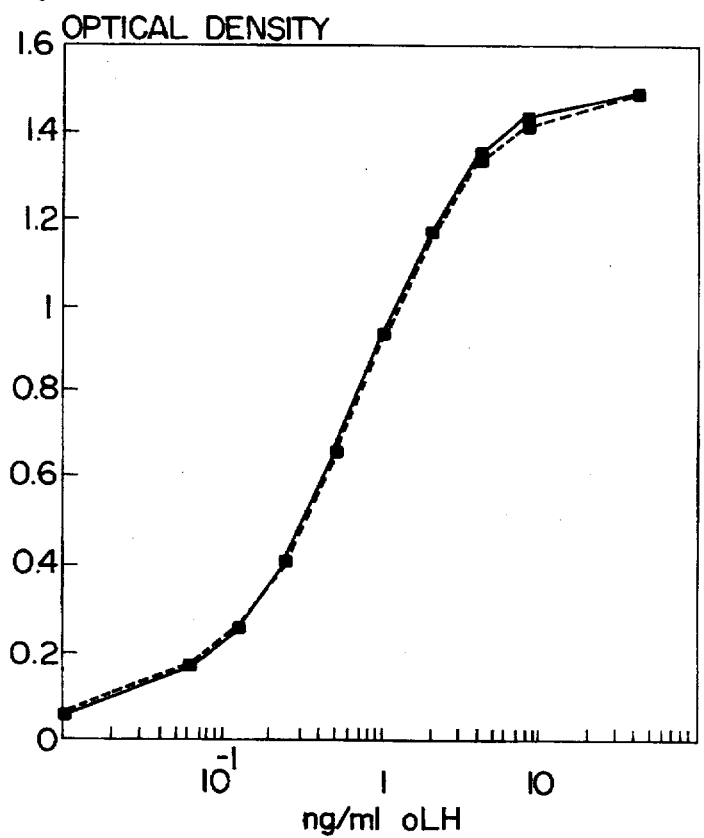
FIG. 4 is a graph plotting optical density as a function of LH concentration which indicates that non-specific interference can be eliminated by carrying out the assay in the presence of INC medium.

FIG. 4 shows the results of such an assay carried out in the presence of INC medium, with a range of concentrations of oLH carried out in PBS-BSA-Tween (--■--) and with a range carried out in LH⁻ (hypophysectomised animal serum) diluted to 1/10th with PBS-BSA-Tween (-■-). The perfect superposition of the two curves indicates that the non-specific interference described hereinabove is completely eliminated. An improvement in the sensitivity of the assay compared to the curve (-■-) in FIG. 3 is also observed.

The effect of the INC medium is the same, whether it is composed of 50% plasma or serum from a hypophysectomised animal.

The proportion of 50% of LH⁻ in the INC medium is not obligatory and can be increased. However, below 50%, the non-specific interference described is not completely eliminated.

Figure 5:
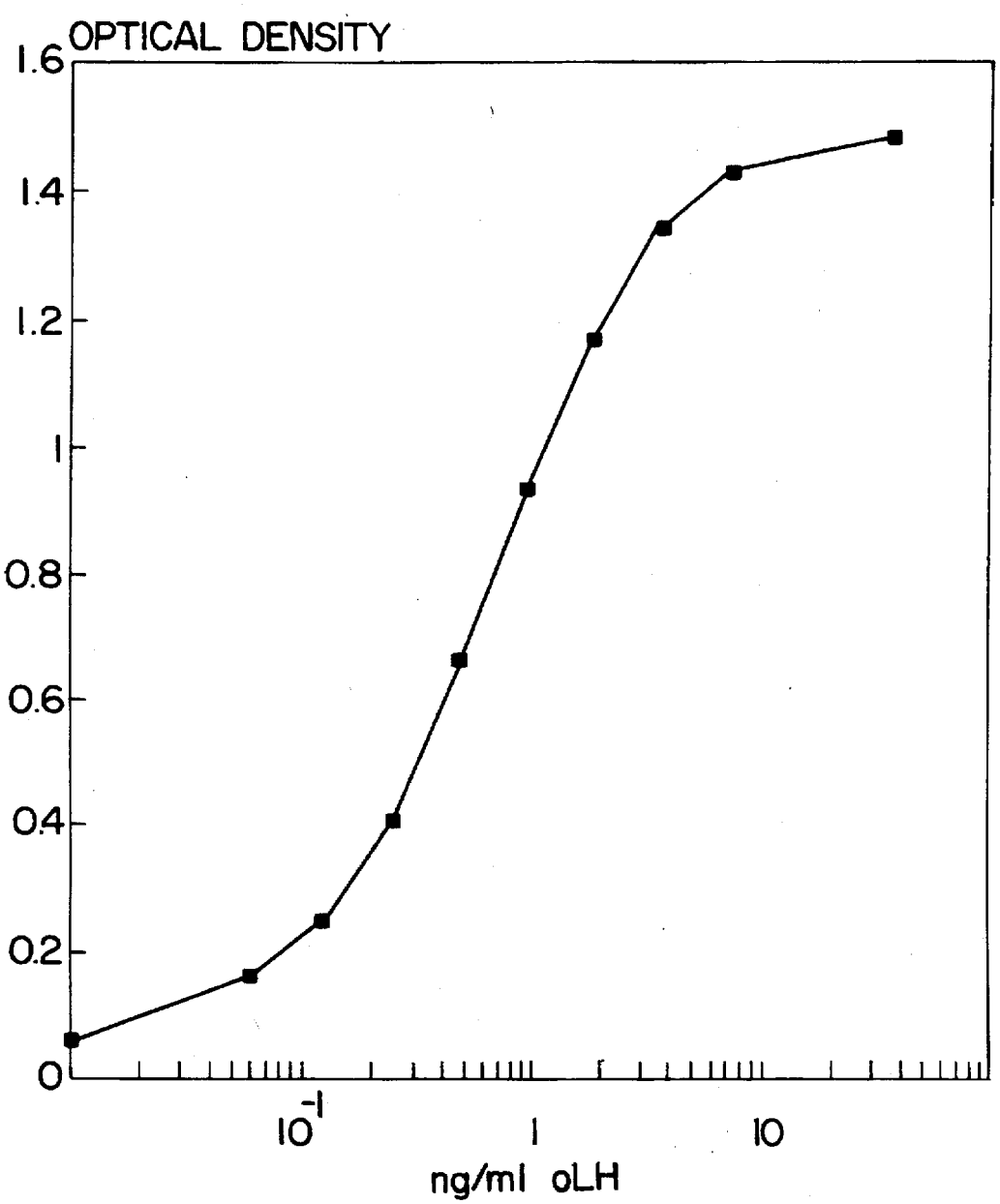
FIG. 5 is a graph plotting optical density as a function of LH concentration in an assay carried out in diluted PBS-BSA-Tween medium.

FIG. 5 illustrates the curve obtained, under these conditions, with a reference range prepared in the dilution medium indicated hereinabove. (FIG. 5 was obtained under the same experimental conditions as the curve (--■--) in FIG. 4). The detection threshold of the assay is 60 pg/ml. The intra-assay coefficient of variation is 2.5% (n=10), the inter-assay coefficient of variation being 6% (n=8).

The protocol detailed hereinabove is a non-limiting embodiment both as regards the concentrations of antibodies and the times of incubation of the substrate, which it is possible to vary. The experimental conditions described hereinabove represent a preferred embodiment for the development of a very sensitive and very reliable assay (little intra- and inter-assay variability), using the lowest possible reagent concentrations.

1.b) Detection of peroxidase with OPD:

OPD can be used as substrate, with the same experimental protocol. 100 μl of substrate are distributed per well; the enzymatic detection is carried out at ambient temperature or at 4° C. for 5 to 20 min; it is stopped with 50 μl of acid solution, as specified hereinabove (C). The reading of the optical density is carried out at 492 nm with the aid of the same type of apparatus.

This assay can also be used in cell culture media, and milk in particular.

EXAMPLE 4

Quantitative fluorimetric assay with the AB2-β-galactosidase system: assay of animal LH.

* Sensitisation of the plates (coating):

The rabbit anti-LH antibody (AB1) is prepared at a concentration of 2.5 μg/ml in 0.1M carbonate buffer, pH 9.6. It is distributed in portions of 100 μl per well. The incubation is carried out for 1 hour at 37° C., then for 18 hours at 4° C.

* Coating or saturation of the wells:

After washing 5 times with PBS-Tween, 100 μl of INC medium are deposited in each well. The incubation is carried out for 30 min at 37° C. The plate is either kept in a dry environment or is used directly.

* Incubation of the samples:

This is carried out in the same way as in the protocol described in Example 3. The duration of incubation can vary from 1 hour to 1 hour 30 min.

* Incubation of the second antibody (horse anti-LH coupled with β-galactosidase, AB2):

After washing the plate, the AB2-β-galactosidase is deposited in portions of 100 μl per well. It was prepared beforehand in the INC medium at a dilution of 1 μg/ml and pre-incubated for 30 min at 37° C.

The incubation in the wells is carried out for 1 hour at 37° C., after which the plate is washed 5 times with PBS-Tween.

* Detection of β-galactosidase with a fluorogenic substrate (4-MUG):

200 μl of MUG prepared in accordance with the instructions given hereinabove at C are deposited in each well. The plate is incubated at 42° C. for 1 to 2 hours. The measurement of the fluorescence is carried out using an automatic fluorimeter for ELISA plates ("Microfluor" from DYNATECH—USA).

Its excitation wavelength is 360 nm; it records at a wavelength of 448 nm.

Figure 6:
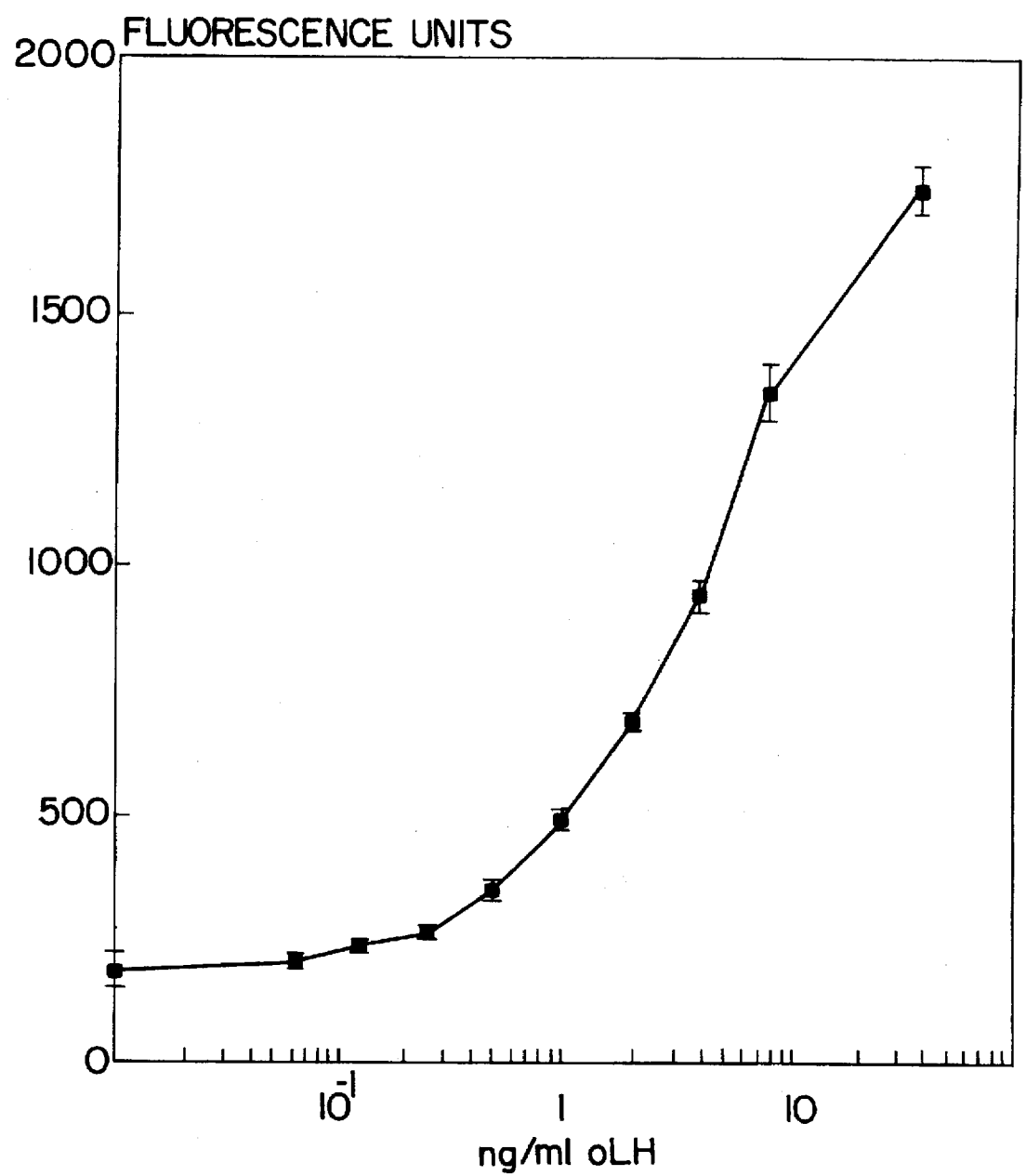
FIG. 6 is a graph plotting florescence as a function of LH concentration showing satisfactory results for an assay conducted in PBS-BSA-Tween-LH.

The results obtained with a reference range prepared in the PBS-BSA-Tween-LH⁻ medium (1/10th) are shown in FIG. 6. The MUG was incubated for 1 hour; it is noted that the detection threshold is less good than in the protocol in Example 3 (between 250 and 500 pg/ml). Moreover, the intra- and inter-assay coefficients of variation are higher in this case. The advantage of this protocol is to allow the assay to be carried out in a shorter time.

The concentrations of reagents were chosen in such a way that the ratio of the quantity of reagents used to the quality of the assay is the most favourable. It is obvious that the concentrations can be modified, while at the same time maintaining a correct assay.

EXAMPLE 5

Assay of animal LH with the AB2-peroxidase system.

It is possible to carry out, under the same conditions as those in Example 4, an assay of LH in which AB2 is coupled to a peroxidase.

EXAMPLE 6

Quantitative and qualitative colorimetric assay of LH, carried out with the AB3-peroxidase system from blood; development of a kit for detection of the LH peak in animals, used in the laboratory or in the field:

The assay based on blood can be used both for quantitative and qualitative purposes; "qualitative assay" is understood as a test which permits the detection of the preovulatory LH peak in the female, in the field, without any measuring apparatus, and which can be simply interpreted with the naked eye. This test likewise permits the detection of LH pulses in the female or in the male.

a) Process for collecting the blood:

An assay carried out on plasma presents a real burden to the extent that it necessitates a centrifugation step, pipetting of the plasma after centrifugation, and its transfer into new tubes and a dilution stage before use in the assay (that is to say pipetting, homogenisation in the dilution buffer).

In order to eliminate this problem, in this test use is made of a new process for taking blood samples from the animals. It consists in placing a very fine needle in the jugular vein of the animal, allowing a blood droplet to form, and applying to it the end of a glass capillary tube, heparinated and calibrated to a very precise volume (10 or 25 µl). The capillary tube must be held horizontally so that the blood can migrate as far as the other end of the capillary tube. Using a small plastic syringe adapted to the diameter of the capillary tube, the contents of the latter are recovered in a tube containing 225 µl of heparinated PBS-Tween-BSA in the case of a capillary tube of 25 µl. The blood is thus diluted 10-fold and has only to be distributed in 2×100 µl in the wells provided in a plate.

This last stage can be avoided by filling all the wells of the plate with 90 µl of heparinated PBS-BSA-Tween. It then suffices to use capillary tubes of 10 µl in volume and to empty each of them directly into one well of the microtitration plate. The sample to be assayed is thus directly diluted and deposited in the plate.

b) Protocol:

* Sensitisation of the plates:

AB1 is diluted to 7.5 µg/ml in 0.1M carbonate buffer, pH 9.6, and incubated for 1 hour at 37° C. then for 18 hours at 4° C. The plates are then washed in PBS-Tween 5 times, then filled with 100 µl of INC medium per well. They are incubated for 30 min at 37° C., emptied, dried, and then sealed under plastic, or used directly.

* Depositing of the samples:

either the 10 µl of blood are deposited directly in the well corresponding to the sample, after first having filled all the wells with 90 µl of heparinated PBS-BSA-Tween;

or 100 µl of the 25 µl of blood diluted in 225 µl of heparinated PBS-BSA-Tween are deposited per well.

The incubation is carried out for 1 hour or less at 37° C. or at ambient temperature. During the incubation the plate is shaken every 15 minutes by tipping it manually in order to rehomogenise the red corpuscles in the liquid phase. 5 washings are then carried out with PBS-Tween if working in the laboratory, or with physiological serum (0.15M NaCl) or with running tap water if working in the field.

* Depositing of the second antibody:

100 µl of AB2 prepared in the INC medium at 5 µg/ml are deposited in each well. The incubation is carried out for 45 min at 37° C. or at ambient temperature. The plate is then washed in accordance with the preceding instructions.

* Depositing of the third antibody:

100 µl of AB3-peroxidase are deposited per well; AB3 was prepared in the INC medium at a dilution of 1/5000th in accordance with the instructions in Example 3.

In the kit in particular AB2 and AB3 will be supplied ready-prepared. After an incubation of 45 min at 37° C. or at ambient temperature, the plate is washed as above and the enzymatic detection is carried out.

c) Reading of the assay with the naked eye, interpretation of the observations:

The ABTS solution (prepared in accordance with the instructions hereinabove at C) and the 2% hydrogen peroxide are mixed only when needed, that is to say just before use. 100 µl of substrate are deposited per well.

The enzymatic reaction is instantaneous and takes place at ambient temperature. After 2 min, the appearance of a green colour in the wells corresponding to a preovulatory LH peak is visible. After 5 min, it is possible to distinguish between the blood samples "carrying" a preovulatory LH peak and the others whose substrate remains colourless.

* This test of the "all or nothing" type is possible by virtue of the combination AB1-AB2 and INC medium, which neutralises any non-specific signal, that is to say the samples with a low LH content, prepared in this protocol, do not result in any colouration of the substrate, in contrast to those with a high LH content which provoke the instantaneous appearance of a green colour.

The INC medium thus avoids the necessity of distinguishing between a more or less light green (in the case of a high non-specific signal, for example) and a dark green (high LH level), with all the risks of variability which this entails. Indeed, the all or nothing character of this test affords a considerable advantage compared to the immunoenzymatic kits marketed for human LH or for other animal hormones.

d) Quantitative assay of LH from blood:

The assay carried out on blood can be both qualitative and also quantitative at one and the same time. It suffices to apply the experimental protocol optimised for the assay, described hereinabove in Example 3, and to take the precaution of "shaking" the plate during the incubation of the blood.

Figure 7:
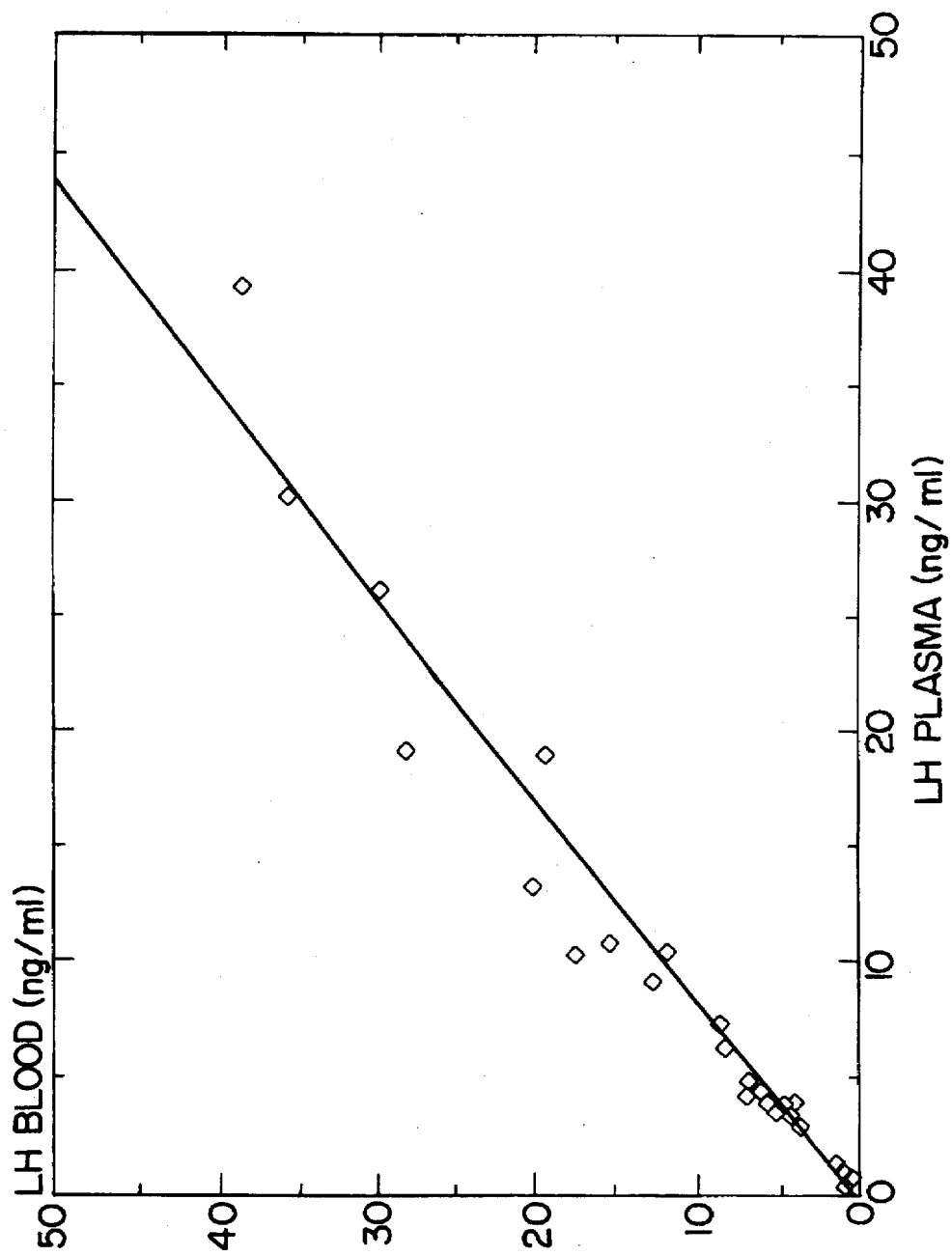
FIG. 7 is a plot of LH blood concentration and LH plasma concentration used to calculate the correlation coefficient therebetween.

The calculation of the coefficient of correlation between the measurement of the LH concentration in the blood and in the plasma originating from the same sample was carried out by comparing the results obtained from both "biological media" (see FIG. 7).

The correlation coefficient=0.9788 (n=40), the equation of the straight regression line: $y=1.14x+0.889$ where Y is the LH concentration (ng/ml) measured in the blood and X is the LH concentration (ng/ml) measured in the plasma in accordance with the protocol described in Example 3.

The value obtained for the correlation coefficient indicates that a very precise quantitative assay based on the blood is entirely possible with the protocol indicated hereinabove.

EXAMPLE 7

Other variants of the test for the detection of animal LH according to the invention:

The simultaneous incubation of AB2 and AB3-peroxidase (1 h) reduces the total duration of the assay.

The tests carried out gave a dose-response curve whose sensitivity was less good than that obtained in accordance with the protocol described hereinabove, but sufficient for the detection of high LH concentrations (15 ng/ml and above). On the other hand, the incubation of the substrate must be longer, 30 to 45 min if necessary, for the detection of preovulatory peaks.

EXAMPLE 8

Detection of the LH peak in the milk of the goat and ewe:
1) In the goat:

The example illustrated here was carried out on a flock of 20 goats synchronised for artificial insemination treatment.

The experimental protocol is the same as that described in Example 3, with the exception that 100 µl of milk are deposited in each well. In this case there is no dilution to carry out, the milk is used raw, not diluted, in contrast to the plasma or the blood.

After eliminating the first spurts of milk, the 100 μl sample can be withdrawn using a calibrated capillary tube, in the same way as in the case of blood. Again, the plate is washed with PBS-Tween or with tap water depending on the location in which the assay is carried out.

Figure 8:
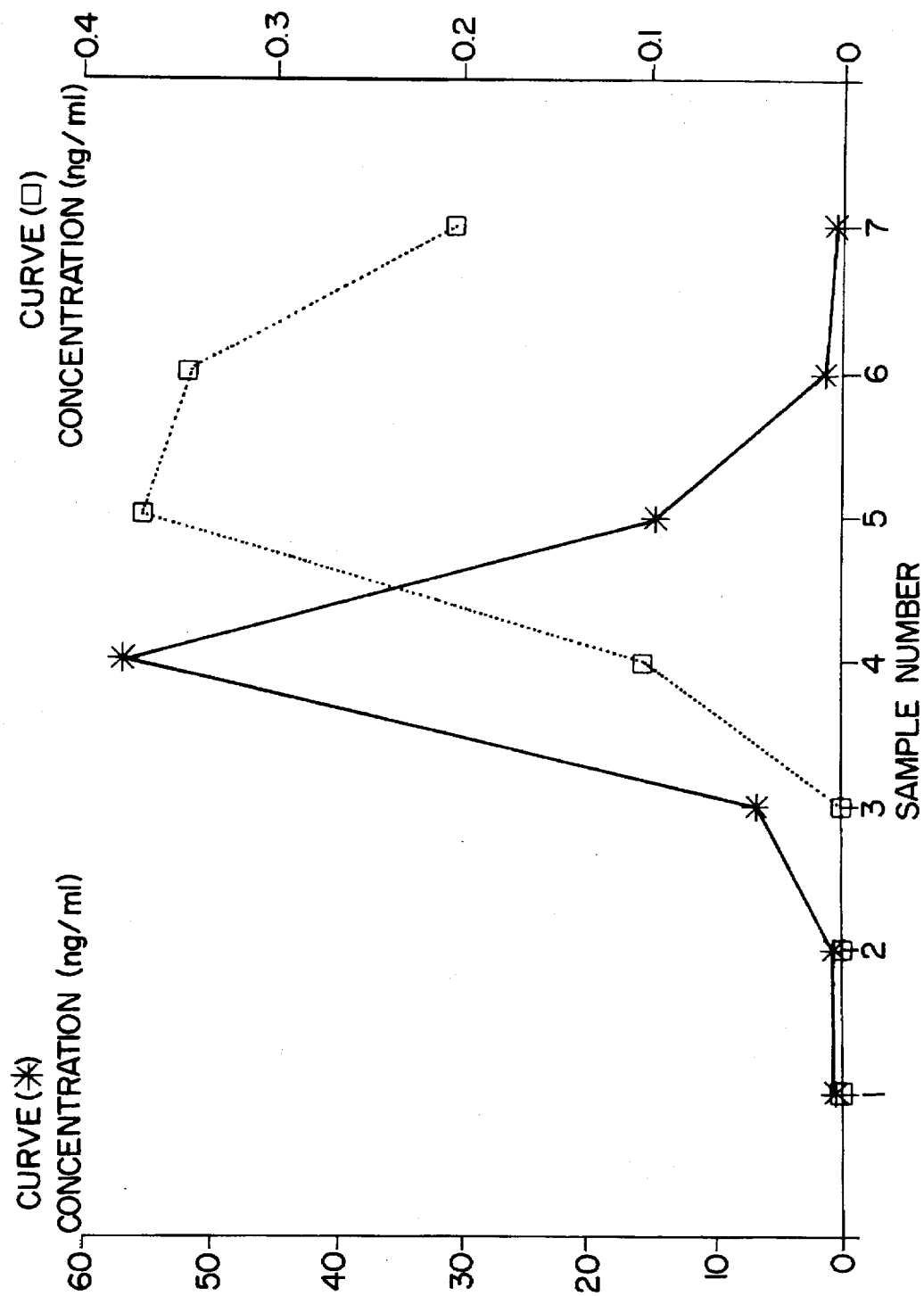
FIG. 8 is a plot showing the profile of secretion of a LH peak in a goat in both blood and milk.

FIG. 8 shows the profile of secretion of the LH peak in a goat, both in the blood (curve -*-) and in the milk (..□..). It is observed that the LH concentrations found in the milk are tiny compared to the plasmatic concentrations. For this reason, it is necessary to use a microtitration plate spectrophotometer. It is noted that the appearance of the LH peak in the milk is 4 hours later than that in the blood, if the start of the peak is used as a comparison point. Table I below shows the LH concentrations measured in the blood and the milk in the course of 7 samplings carried out every 4 hours in the two media simultaneously. The comparison of the results shows that the appearance of the LH peak in the milk is later 4 or 8 hours than that in the blood, if the peak maximum is compared. The start of the peak, in contrast, is always 4 hours later in the milk than in the blood, and this in a constant manner. Apart from the preovulatory peak, the LH concentrations in the milk are not detectable.

This Table I clearly illustrates the importance of the implementation of the process according to the invention in controlling reproduction within goat herds, but also, and in a more general manner, for all the species in it which can be used (bovine, ovine, etc.). It makes it possible to eliminate those females who have not had a preovulatory peak (who have thus not ovulated) and to fertilise at an optimum time those females who have shown an early preovulatory peak. This permits the drawing-up of insemination plans, such as plan III hereinbelow, which is very useful especially for maximising the profitability of the artificial insemination programmes carried out in the different animal species in question.

TABLE I

Detection of the LH peak in the blood and milk of the goat

| Goat No. | Samples | | | | | | | | | | | | | |
|---|---|---|---|---|---|---|---|---|---|---|---|---|---|---|
| | n* 1 Blood | Milk | n* 2 Blood | Milk | n* 3 Blood | Milk | n* 4 Blood | Milk | n* 5 Blood | Milk | n* 6 Blood | Milk | n* 7 Blood | Milk |
| 1 | 0.10 | ND | 0.30 | ND | 0.34 | ND | 33.50 | ND | 24.00 | 0.058 | 1.20 | 0.125 | 0.60 | 0.093 |
| 3 | 0.10 | ND | 0.20 | ND | 0.15 | ND | 0.28 | ND | 46.14 | 0.050 | 8.85 | 0.136 | 0.86 | 0.160 |
| 5 | 0.92 | ND | 0.50 | ND | 1.03 | ND | 53.90 | ND | 35.45 | 0.231 | 2.37 | 0.319 | 0.83 | 0.148 |
| 6 | 0.30 | ND | 0.29 | ND | 1.02 | ND | 1.57 | ND | 54.30 | 0.080 | 5.88 | 0.157 | 0.86 | 0.119 |
| 7 | 0.60 | ND | 0.38 | ND | 6.91 | ND | 57.00 | 0.104 | 14.66 | 0.370 | 1.50 | 0.346 | 0.54 | 0.205 |
| 8 | 0.30 | ND | 0.32 | ND | 0.52 | ND | 1.07 | ND | 15.13 | ND | 24.18 | 0.043 | 1.75 | 0.120 |
| 10 | 0.21 | ND | 0.23 | ND | 0.37 | ND | 0.98 | ND | 44.68 | ND | 41.73 | 0.142 | 2.12 | 0.197 |
| 11 | 0.10 | ND | 0.10 | ND | 0.23 | ND | 60.00 | 0.050 | 11.43 | 0.163 | 1.20 | 0.200 | 0.65 | 0.433 |
| 14 | 0.80 | ND | 0.72 | ND | 0.65 | ND | 3.28 | 0.050 | 29.55 | 0.060 | 43.08 | 0.090 | 2.21 | 0.210 |
| 15 | 0.23 | ND | 0.36 | ND | 0.20 | ND | 1.71 | ND | 17.30 | ND | 39.63 | 0.117 | 2.19 | 0.257 |
| 16 | 1.51 | ND | 1.32 | ND | 1.78 | ND | 1.10 | ND | 1.03 | ND | 0.80 | ND | 0.48 | ND |
| 17 | 0.30 | ND | 0.54 | ND | 0.60 | ND | 3.47 | ND | 45.42 | 0.056 | 6.17 | 0.271 | 0.20 | 0.185 |
| 18 | 0.30 | ND | 0.36 | ND | 0.68 | ND | 49.59 | ND | 19.96 | 0.114 | 2.75 | 0.197 | 0.30 | 0.097 |
| 20 | 0.16 | ND | 0.27 | ND | 57.90 | ND | 17.39 | 0.099 | 2.92 | 0.106 | 0.57 | 0.009 | 0.11 | 0.050 |

ND: not detectable
The concentrations are given in ng/ml

PLAN III
VARIABILITY OF THE INTERVAL: END OF TREATMENT ⟷ LH PEAK

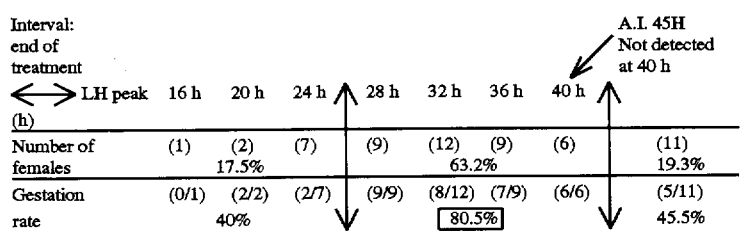

| Interval: end of treatment ⟷ LH peak (h) | 16 h | 20 h | 24 h | 28 h | 32 h | 36 h | 40 h | A.I. 45H Not detected at 40 h |
|---|---|---|---|---|---|---|---|---|
| Number of females | (1) | (2) 17.5% | (7) | (9) | (12) 63.2% | (9) | (6) | (11) 19.3% |
| Gestation rate | (0/1) | (2/2) 40% | (2/7) | (9/9) | (8/12) 80.5% | (7/9) | (6/6) | (5/11) 45.5% |

2) In the ewe:

The example illustrated here was carried out on a flock of 12 Lacaune milking ewes chosen from among the "good" milkers.

These females received a synchronisation treatment (fluorogestone acetate) for 14 days, after which they received an injection of 500 I.U. of eCG (ovary-stimulating hormone).

The samples of blood and milk were taken every four hours, as from the detection of oestrus behaviour. Nine samples were thus taken from each female over a period of 32 hours.

The measurement of the LH concentration was carried out in the two media, blood and milk, in accordance with the experimental protocol described in Example 3 hereinabove.

Table II hereinbelow expresses the results in ng/ml and shows a perfect interval of four hours between the LH peak in the blood and that detected in the milk, in which, apart from the preovulatory peak, the LH concentrations are not detectable.

TABLE II

Detection of the LH peak in the blood and milk of ewes

| Milk prod./day | Ewe No. | n° 1 Blood | n° 1 Milk | n° 2 Blood | n° 2 Milk | n° 3 Blood | n° 3 Milk | n° 4 Blood | n° 4 Milk | n° 5 Blood | n° 5 Milk |
|---|---|---|---|---|---|---|---|---|---|---|---|
| 0.98 | 1 | 1.61 | — | 1.66 | — | 1.59 | — | 27.11 | — | <u>34.37</u> | 0.62 |
| 1.62 | 2 | 0.95 | — | 2.27 | — | 35.00 | 0.0 | <u>39.65</u> | 0.6 | 6.9 | <u>0.97</u> |
| 1.82 | 3 | 0.7 | — | 1.5 | — | <u>25.67</u> | — | 12.23 | <u>0.24</u> | 1.74 | 0.2 |
| 1.94 | 4 | 0.49 | — | 0.34 | — | <u>36.22</u> | — | 7.15 | <u>0.19</u> | 1.29 | 0.17 |
| 1.3 | 5 | 0.57 | — | 0.16 | — | 0.36 | — | 0.99 | — | <u>37.00</u> | — |
| 1.94 | 6 | 0.58 | — | 0.52 | — | 0.66 | — | 1.69 | — | <u>18.28</u> | — |
| 1.76 | 7 | 0.18 | — | 0.23 | — | <u>19.5</u> | — | 8.5 | <u>0.25</u> | 1.2 | 0.26 |
| 1.26 | 8 | 0.27 | — | 0.33 | — | 0.3 | — | 0.4 | — | <u>23</u> | — |
| 1.68 | 9 | 0.30 | — | <u>36.8</u> | — | 14.00 | <u>0.32</u> | 1.72 | 0.22 | 0.68 | 0.18 |
| 1.54 | 10 | 2.4 | — | 3.76 | — | <u>37.96</u> | 0.08 | 38.31 | <u>0.41</u> | 6.88 | 0.38 |
| 0.98 | 11 | 0.37 | — | 0.55 | — | <u>26.86</u> | 0.06 | 4.23 | <u>0.18</u> | 6.14 | 0.12 |
| 1.18 | 12 | 2.31 | — | <u>37.1</u> | 0.15 | 16.66 | <u>0.21</u> | 6.36 | 0.19 | 1.13 | 0.11 |

— Milk production/day

| Milk prod./day | Ewe No. | n° 6 Blood | n° 6 Milk | n° 7 Blood | n° 7 Milk | n° 8 Blood | n° 8 Milk | n° 9 Blood | n° 9 Milk |
|---|---|---|---|---|---|---|---|---|---|
| 0.98 | 1 | 4.32 | <u>0.88</u> | 1.22 | 0.58 | 0.97 | 0.23 | 0.98 | 0.14 |
| 1.62 | 2 | 1.41 | 0.7 | 1.05 | 0.31 | 0.61 | 0.09 | 0.31 | 0.07 |
| 1.82 | 3 | 0.9 | 0.2 | 0.5 | 0.06 | 0.55 | — | 0.56 | — |
| 1.94 | 4 | 0.55 | 0.15 | 0.2 | 0.03 | 0.2 | — | 0.2 | — |
| 1.3 | 5 | 14.4 | <u>0.4</u> | 2.66 | 0.4 | 1.38 | 0.31 | 0.23 | 0.21 |
| 1.94 | 6 | 9.3 | <u>0.23</u> | 1.07 | 0.17 | 0.45 | 0.13 | 0.3 | 0.08 |
| 1.76 | 7 | 0.3 | 0.12 | 0.2 | — | 0.15 | — | 0.25 | — |
| 1.26 | 8 | 15 | 0.42 | 2.15 | 0.41 | 0.2 | 0.3 | 0.12 | 0.15 |
| 1.68 | 9 | 0.25 | 0.09 | 0.31 | 0.08 | 2.57 | — | 0.31 | — |
| 1.54 | 10 | 3.26 | 0.19 | 2.45 | 0.13 | 0.37 | 0.08 | 2.1 | — |
| 0.98 | 11 | 1.04 | 0.09 | 0.47 | 0.08 | 0.49 | 0.07 | 0.48 | — |
| 1.18 | 12 | 0.66 | 0.9 | 0.72 | 0.08 | 0.74 | — | 0.67 | — |

— Milk production/day

LH: values in ng/ml
Values underlined: maximum value of the LH peak in the blood and in the milk The detection of the LH peak in the milk affords several advantages:

its duration is longer than in the blood (20 to 24 hours as opposed to 8 to 12 hours in the blood), which means that fewer samples need to be taken, and the interval between each sample can be greater (for example every eight hours);

a milk sampling is less "stressful" than a blood sampling and can be carried out at the time when the animals are being milked;

moreover, in the case of ewes, the test using milk can be read off with the naked eye.

Figure 16:
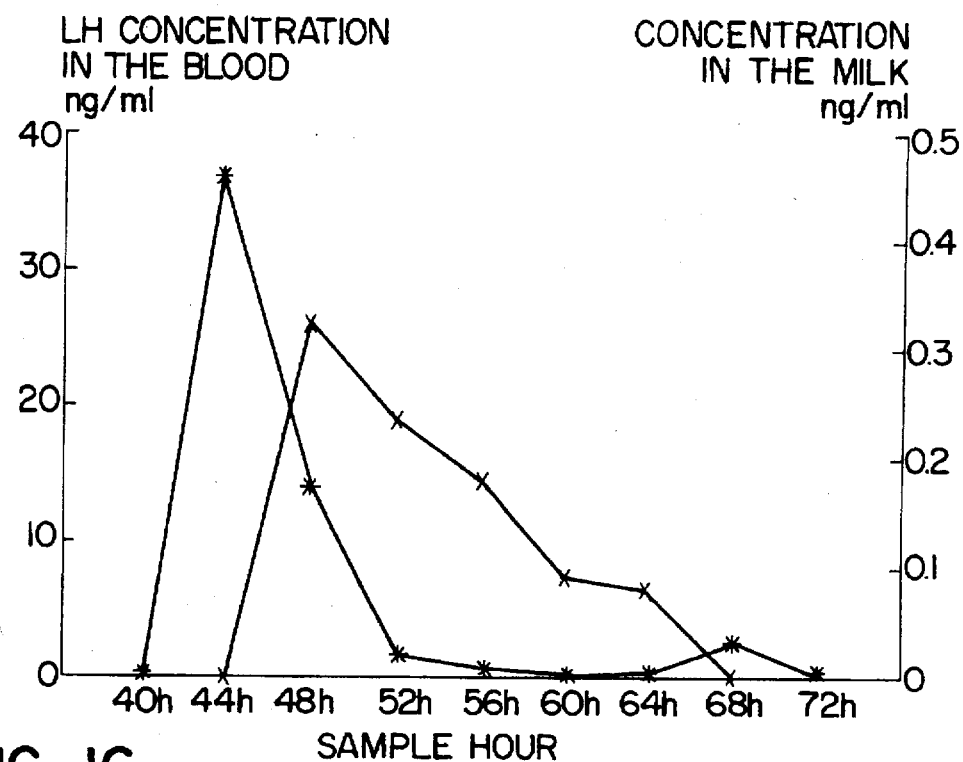
FIG. 16 is a profile of secretion of the LH peak in a ewe both in blood and milk.

FIG. 16 shows the profile of secretion of the LH peak in ng/ml, as a function of time, in a ewe, both in the blood (curve -*-) and in the milk (-X-).

EXAMPLE 9

Applications in the field:

These examples are illustrated by plates and are supported by a study of the correlation between the concentrations obtained by the ELISA and those obtained by a radioimmunological assay carried out in the plasma.

a) Detection of preovulatory LH peaks in superovulated ewes (FIGS. 9A and B):

The FIGS. 9 are photos of plates comprising 12 columns designated 1 to 12, and 8 rows designated A to H.

Columns 1 and 2 correspond to the reference range of the concentrations, and columns 3 to 11 correspond to the samples taken from eight ewes.

Figure 9A:
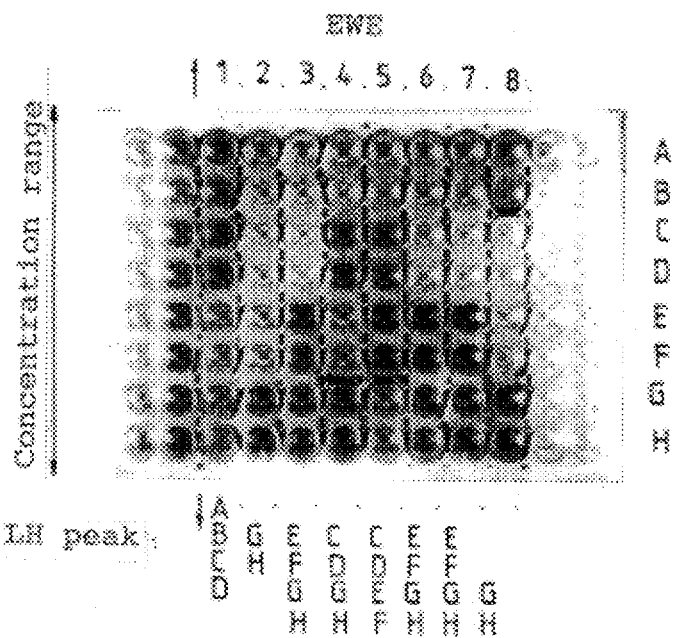
FIGS. 9A and 9B are photos of plates obtained by an ELISA procedure used to detect pre-ovulatory LH peaks in superovulated ewes.
Figure 9B:
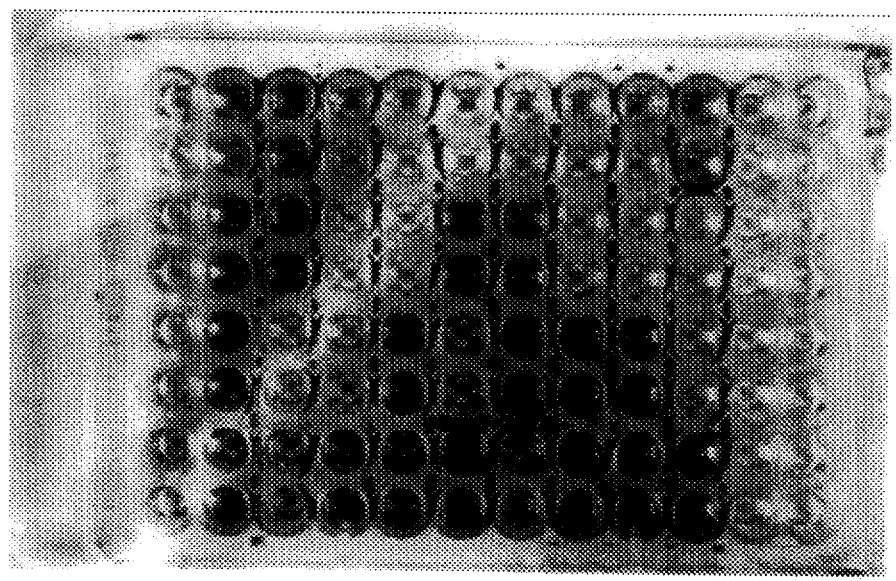

FIG. 9A shows the order of deposition of the samples. The samples from one female are deposited in a column (columns 3 to 11): each sample is double-assayed. The LH peaks "appear" as a dark green, which in this figure and in the following figures is represented by a dark grey, as can be seen in detail in FIG. 9B, in which the reference range of concentrations is also deposited on the left of the plate in 2 columns (columns 1 and 2).

The samples were taken every 4 hours starting from the onset of heat. For ewe 1 (column 3), a peak is observed in the first two samples (wells $A_3$–$B_3$ and $C_3$–$D_3$).

This assay was carried out on plasma. The detection time was 15 min at ambient temperature.

Figure 10:
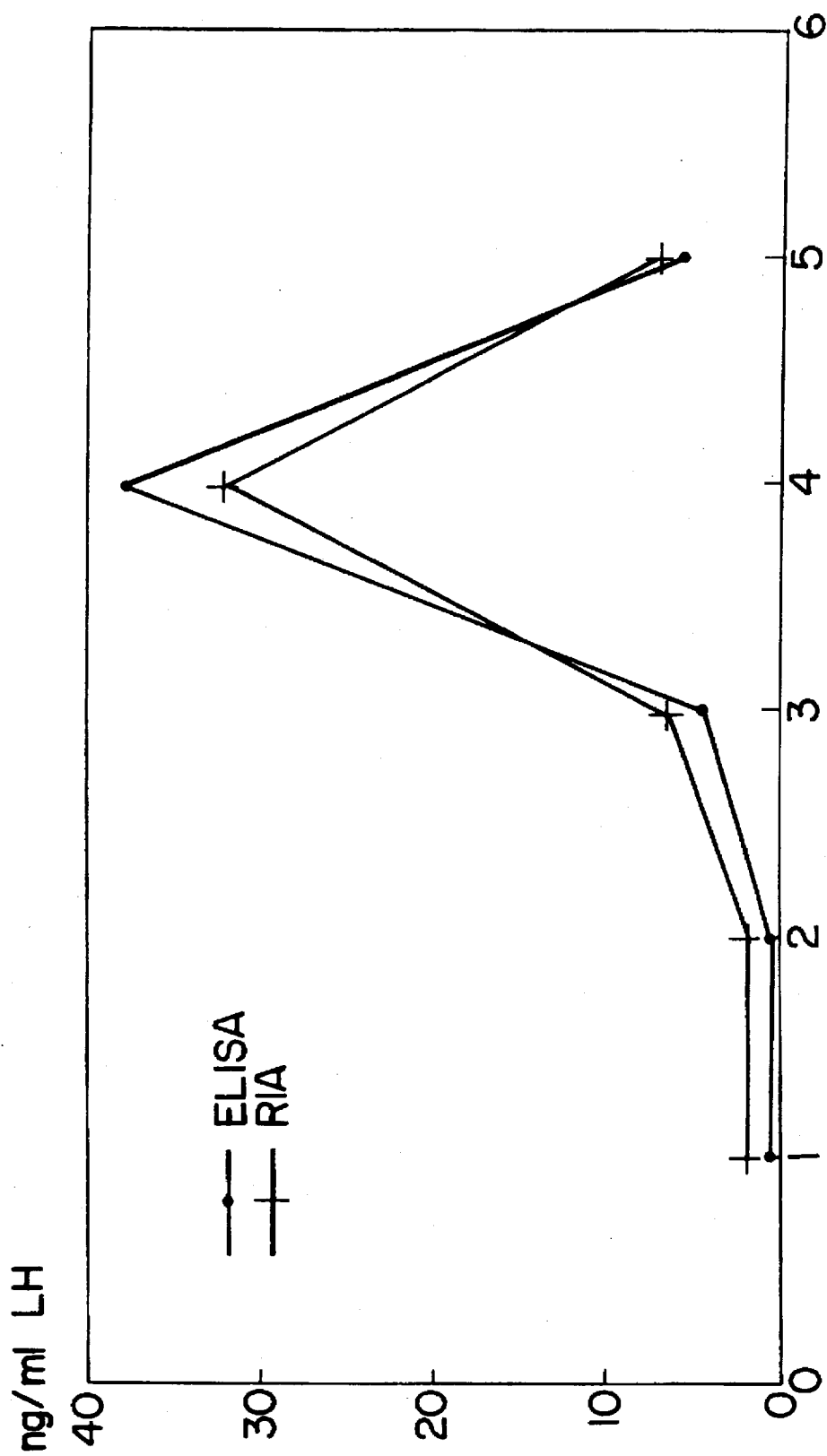
FIG. 10 is an LH secretion profile obtained in a ewe by both ELISA and by RIA on plasma.

FIG. 10 illustrates a LH secretion profile obtained in a ewe (Example 3) by ELISA (AB3-peroxidase/ABTS) and by RIA (radioimmunoassay) on plasma.

b) Detection of preovulatory peaks in superovulated goats (FIG. 11):

This figure shows a photo of a plate of the same type as the previous one (columns 1 to 12, rows A to H).

Samples were taken every 4 hours after the onset of heat.

The assays were carried out on blood. The detection time was 10 min at ambient temperature.

Figure 12A:
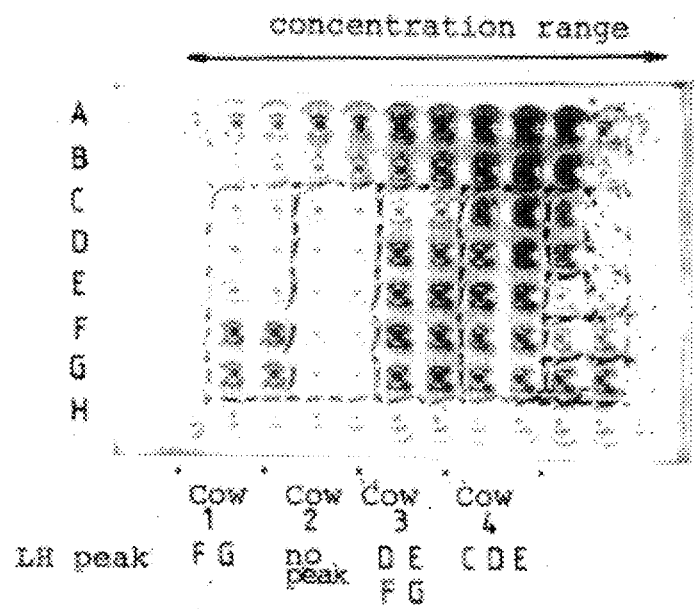
FIGS. 12A and 12B are photos of plates used in an ELISA procedure to detect pre-ovulatory peaks in cows.
Figure 12B:
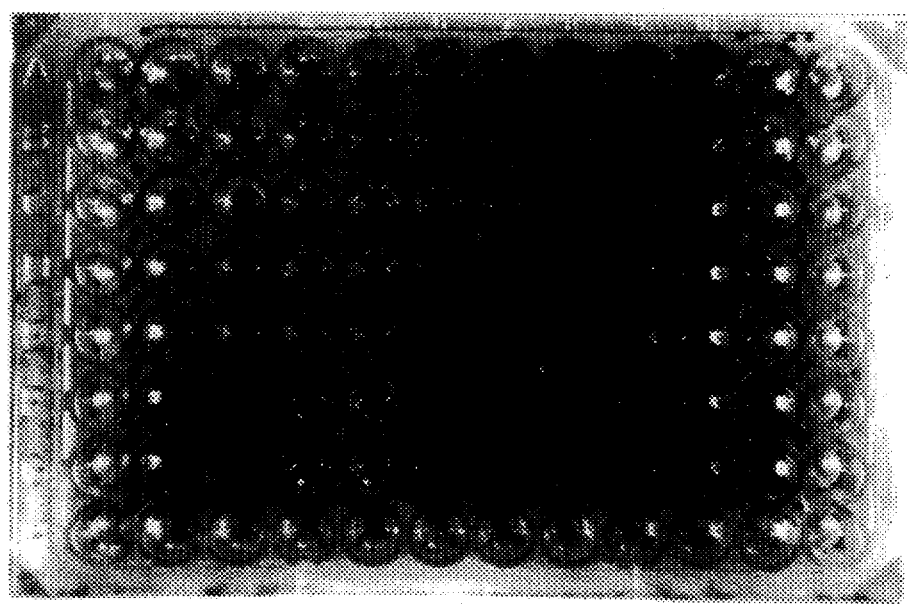

The samples were deposited in columns by animal: column 2 shows, for example, a peak in wells $D_2$–$E_2$ then the end of the peak in $F_2$. The summit of the peak is in $D_2$. Outside the peaks, the substrate remains colourless. In column 6, the maximum of a peak is again observed in $D_6$–$E_6$, then the end of the peak in $F_6$.

c) Detection of preovulatory peaks in cows (FIG. 12):

After injection of GnRH, samples were taken from the animals every 30 minutes. The samples were double-assayed and deposited in columns (cow 1: columns 2 and 3; cow 2: columns 4 and 5; cow 3: columns 6 and 7; cow 4: columns 8 and 9). The reference range is deposited in the first two rows A and B (FIG. 12A).

The assay is carried out on blood. The detection time is 5 min in FIG. 12A and 15 min in FIG. 12B at ambient temperature. The absence of an LH peak in cow 2 is observed, and the start of a LH peak in the 4th and 5th samples ($F_2$–$F_3$/$G_2$–$G_3$) in cow No. 1. In the two following animals, the peak appeared more quickly: in the second sample ($D_6$–$D_7$) for cow No. 3 and in the first sample ($C_8$–$C_9$) for cow No. 4. In the case of the latter, the fall in the peak is very clearly observed.

Figure 13:
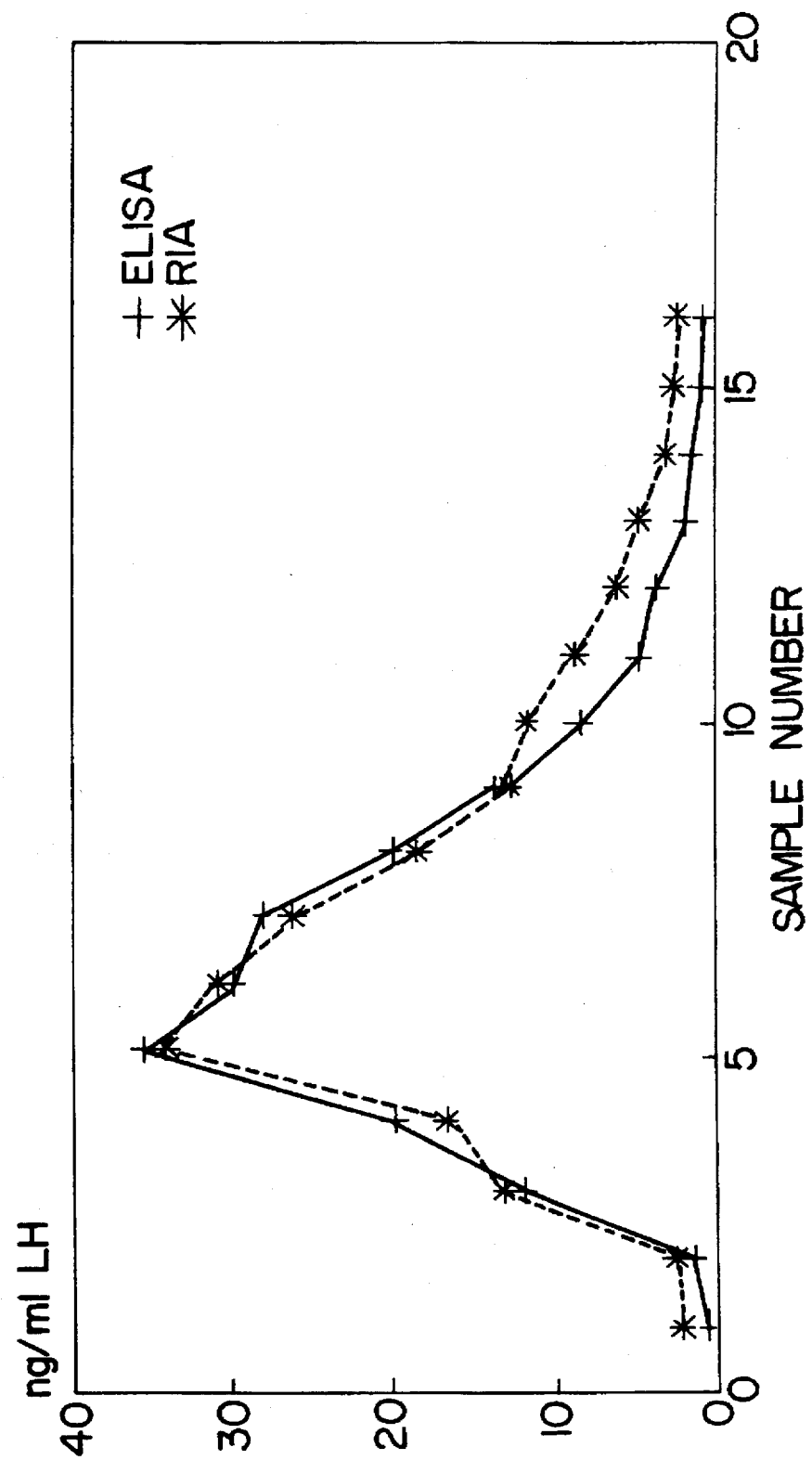
FIG. 13 is an overall profile of LH secretion in a cow treated with Gnrh.
Figure 14A:
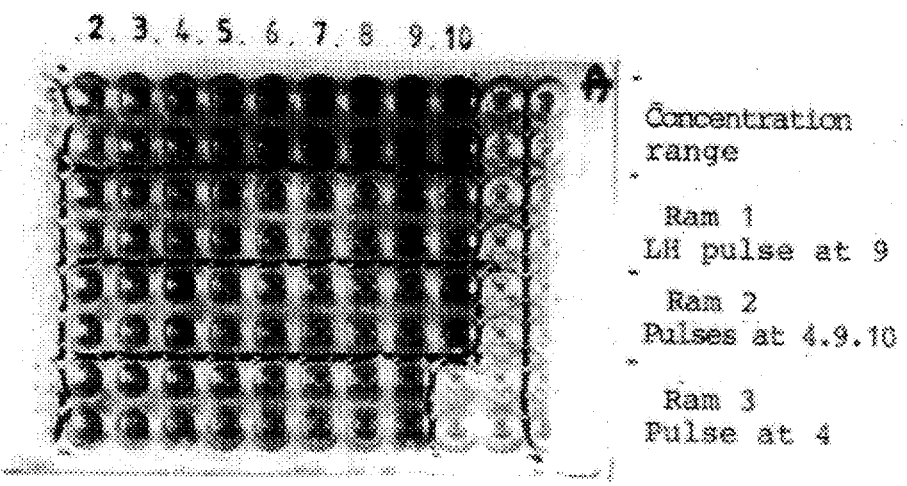
FIGS. 14A and 14B are photos of plates used in an ELISA assay studying the micropulsatility in ram LH.
Figure 14B:
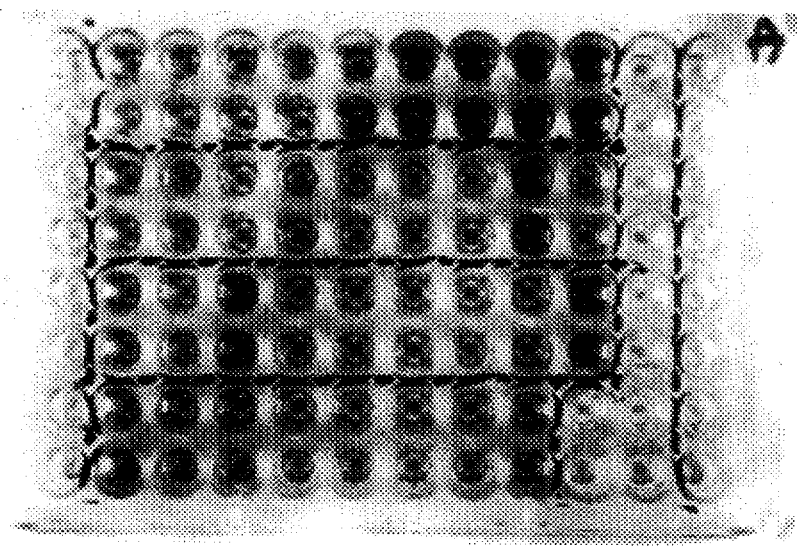

FIG. 13 shows the overall profile of LH secretion in a cow treated with GnRH. A superposition of the concentrations measured by ELISA and by RIA can be observed.

d) Study of the micropulsatility in rams (FIG. 14):

The assays were carried out in the plasma in accordance with the protocol in Example 3. The samples were taken every 20 minutes. They are deposited in rows (ram 1: rows C and D; ram 2: rows E and F; ram 3: rows G and H) and are assayed in duplicate (duplicates are arranged vertically).

The detection time is 30 minutes. The pulse at $C_9$–$D_9$ is observed for ram No. 1, at $E_4$–$F_4$ and $E_{10}$–$F_{10}$ for ram No. 2, and a very slight pulse at $G_4$–$H_4$ for ram No. 3, and at $E_9$–$F_9$ for animal No. 2.

Figure 15:
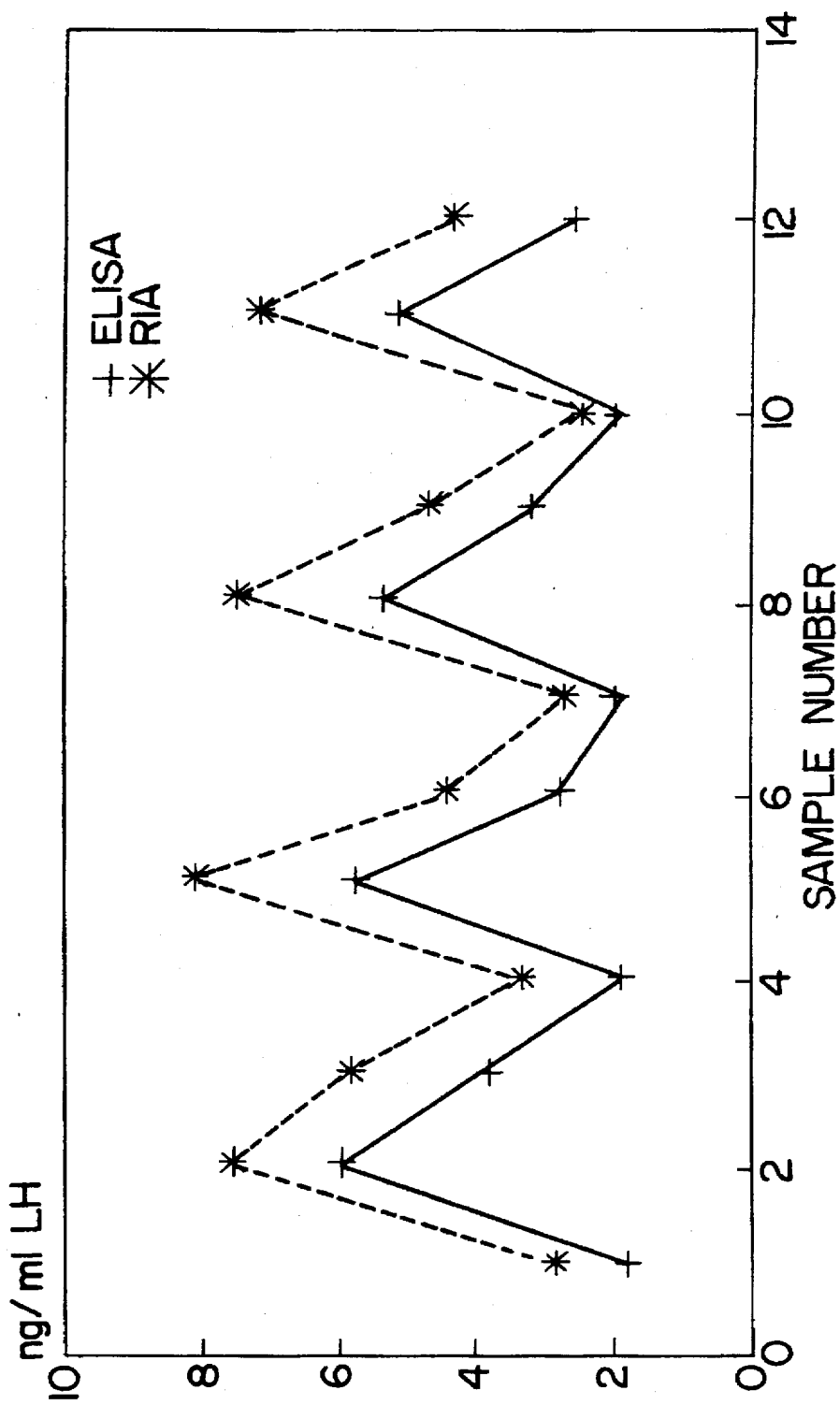
FIG. 15 is an LH secretion profile obtained in a ram using both ELISA and RIA procedures.

FIG. 15 illustrates an LH secretion profile obtained in the ram using ELISA and RIA. The concentrations obtained using ELISA have absolute values lower than those using RIA, but the profile is identical. This difference is due to the better sensitivity of ELISA, which permits detection of lower values than does RIA.

e) Calculation of the correlation coefficient obtained between assays carried out by ELISA and assays by RIA:

The RIA used is that published by J. PELLETIER et al., 1982.

1) Correlation in the bovine species: (n=60)
   correlation coefficient: r=0.9705
   equation of the straight regression line: y=1.09x−0.971.

2) Correlation in the caprine species: (n=60)
   correlation coefficient: r=0.9759
   equation of the straight regression line: y=1.031x−0.978.

3) Correlation in the ovine species (n=67)
   correlation coefficient: r=0.9808
   equation of the straight regression line: y=1.0745x−2.45
   where Y is the LH concentration (ng/ml) measured by ELISA
   X is the LH concentration (ng/ml) measured by RIA.

EXAMPLE 10

Detection of the LH peak in the doe.

Figure 17:
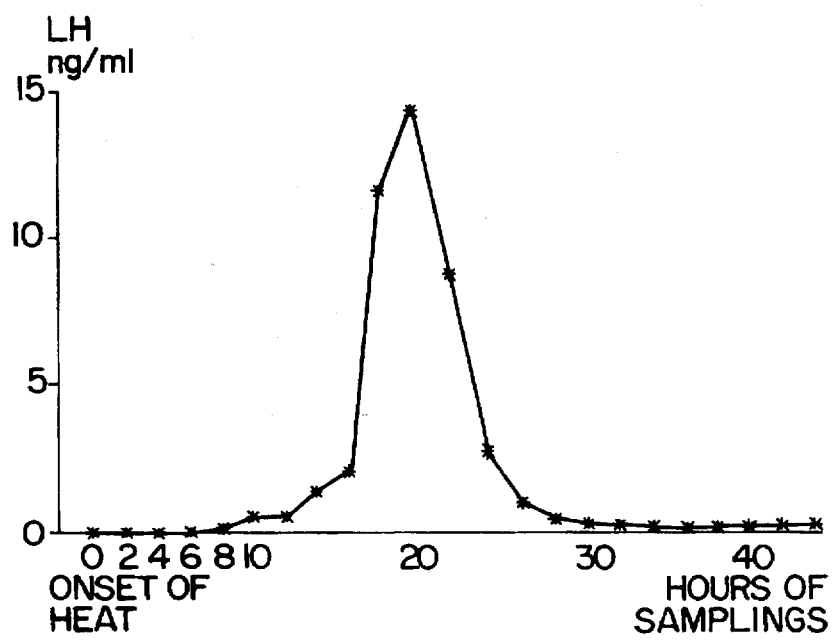
FIG. 17 is an LH secretion profile for one doe.

Assays were carried out on blood samples taken every two hours, during the whole of the period of heat, from the New Caledonia Rusa doe. The samples were taken from seven does and the assays were carried out as described in Example 3. The tests were read by the naked eye, as for the other species. FIG. 17 shows the LH secretion profile in ng/ml as a function of time in one doe (doe No. 80). The results obtained in all the females once again show that the time of the LH peak is very variable during the period of heat: in general, it occurs at the onset of heat.

This clearly illustrates the importance of the process according to the invention for being able to establish with precision the time of insemination, given the variability in the appearance of the LH peak.

It may be noted in particular that this process is of interest in the artificial insemination of embryo-donating females in breeds of the Cervidae family which is becoming extinct.

EXAMPLE 11

Detection of the LH peak in the bitch.

Figure 18:
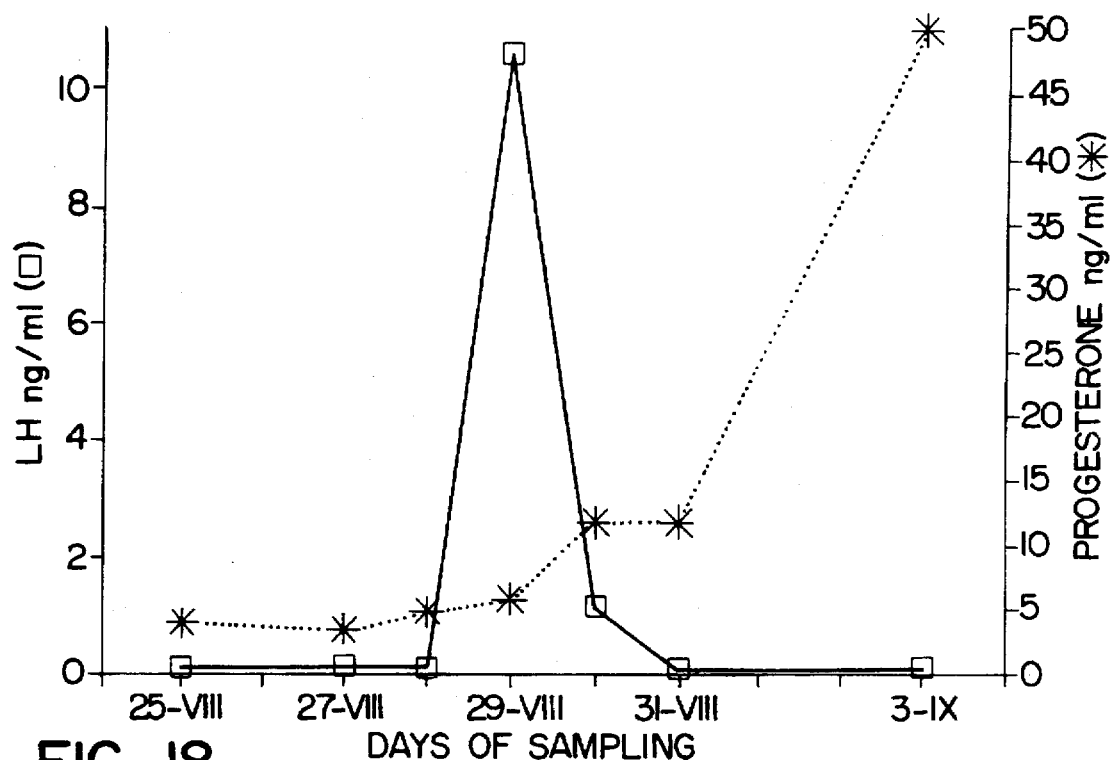
FIG. 18 is a secretion profile for LH and progesterone in a bitch.

The assays were carried out as described in Example 3, using daily blood samples taken from two bitches during the period of heat. In the bitch, the preovulatory LH peak extends over a greater period of time than in the other species described: the duration is 24 hours on average. For this reason, it can be detected taking only one sample of blood daily, which represents an advantage for the clients of a veterinary practice. The results obtained with the "DIXIE" bitch and illustrated in FIG. 18 show this clearly. The tests are read with the naked eye, as for the other species.

FIG. 18 shows the secretion profile for LH (-□-) and for progesterone (-*-) in ng/ml obtained in the DIXIE bitch.

It is observed that, beyond 48 hours after the preovulatory peak (3.9.90), the progesterone content considerably increased (>50 ng/ml). This is proof of the presence of a corpus luteum (responsible for the high progesterone secretion) which results from ovulation.

Given the length of the period of heat in the bitch, the kit will make it possible to establish with precision the time of ovulation in the bitch in question and will allow insemination to be carried out at the optimum time (fertilisation takes place 48 hours after ovulation in the bitch). Once again, it will be possible for an insemination plan to be drawn up precisely, with the aid of the process according to the invention.

EXAMPLE 12

Detection of the LH peak in the sow.

A correlation was established between the LH concentration values established by a radioimmunological assay and those obtained with the process according to the invention, carried out in accordance with the protocol in Example 3. The assays were carried out on sow plasma.

correlation coefficient n=0.943 equation of the straight regression line: y=0.1719x+0.069 (n=20), where:

y is the LH concentration (ng/ml) measured by ELISA; and x is the LH concentration (ng/ml) measured by RIA.

Figure 19:
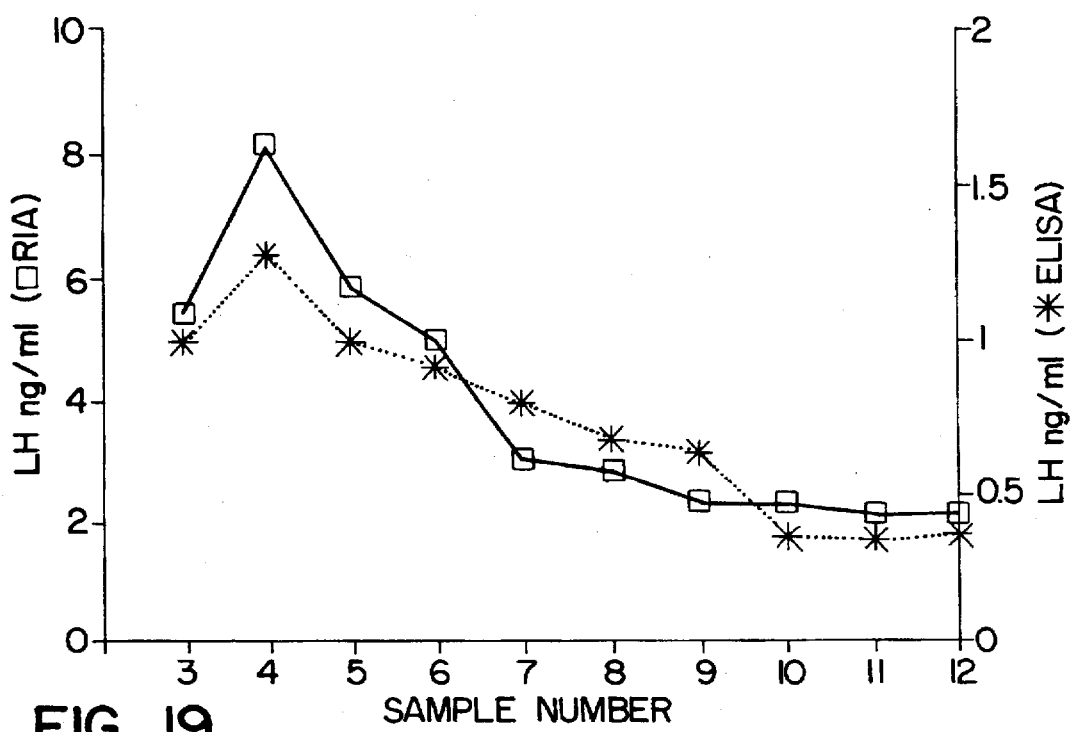
FIG. 19 is an LH secretion profile in a ram conducted with an assay according to the invention and with RIA.

FIG. 19 illustrates an LH secretion profile in ng/ml obtained with an assay according to the invention (-*-) and with a RIA (-□-).

EXAMPLE 13

Assay of ovine FSH using the process according to the invention.

a—Antibodies used for the assay:

the first antibody ($AB_1$) is a monoclonal antibody specific to the β-subunit of the FSH of numerous species (bovine, ovine, equine, porcine, human, murine, canine, rabbit and ostrich). It was kindly supplied by Professor Jacques LUSSIER for these experimental tests. This monoclonal antibody was produced by Professor LUSSIER and his team (University of Montreal, Faculty of Veterinary Medicine, CRRA, CP 5000, St. Hyacinthe J297C6, Quebec). This is a monoclonal antibody of type IgG1;

the second antibody ($AB_2$) is a polyclonal antibody specific to ovine FSH, which was produced in the rabbit. It is produced by and is available from the Department of Physiology of Reproduction, INRA, 37380 NOUZILLY;

the third antibody ($AB_3$) is a polyclonal antibody marketed by Jackson Laboratories (USA). It is a rabbit anti-IgG antibody linked to peroxidase and produced in the goat—reference 111-035-003.

b—Experimental protocol:

The protocol used is that presented in Example 3:

(1) The first antibody is prepared in 0.1M carbonate buffer, pH 9.6, at a concentration of 7.5 µg/ml. 100 µl are distributed per well. The incubation times for the sensitisation of the plates are the same: 1 hour at 37° C. and 18 hours at 4° C.

(2) The washings and the saturation of the wells ("coating") are carried out in the same way as in Example 3.

(3) The incubation of the samples and of the range: same process as in Example 3, the ovine FSH range (NIH standard: oFSH-13-AFP-2846-C) is prepared in PBS-Tween-BSA containing serum from a hypophysectomised animal diluted to 1/10th. It comprises the concentrations: 125 pg/ml, 250 pg/ml, 500 pg/ml, 1 ng/ml, 2 ng/ml, 4 ng/ml, 8 ng/ml and 40 ng/ml. It is deposited double, 100 µl per well. The plasmas to be assayed are diluted ten-fold in PBS-Tween-BSA. The duration of incubation is one hour at 37° C.

(4) Washings identical to those in Example 2.

(5) Preparation and incubation of the second antibody ($AB_2$), anti-ovine FSH. It is prepared in the INC medium at a concentration of 5 µg/ml. Its preparation is effected in the same way as in Example 3. The incubation time is one hour at 37° C.

(6) Washings identical to those in Example 3.

(7) Preparation and incubation of the third rabbit anti-IgG antibody ($AB_3$) linked to peroxidase. It is prepared in accordance with the protocol in Example 3 at a dilution of 1/5000th (in accordance with the manufacturer's instructions). Incubation time one hour at 37° C.

(8) Washings identical to those in Example 3.

(9) Depositing of the substrate of peroxidase and reading of the optical density.

Figure 20:
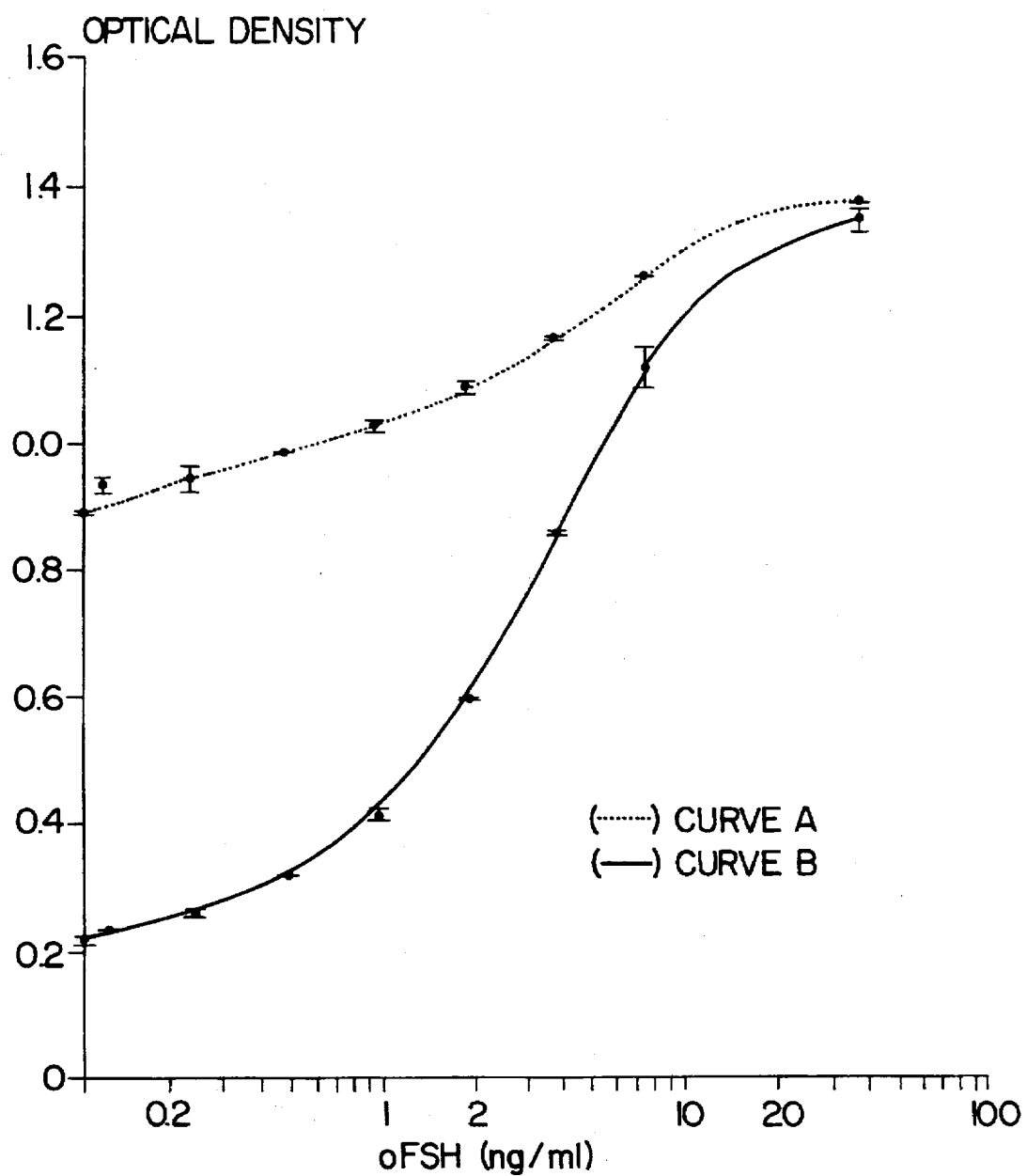
FIG. 20 is a plot of optical density as a function of oFSH concentration carried out and with INC medium.

(c) Results:

* FIG. 20 shows the results of such an assay carried out in accordance with INC protocol (curve B). The detection threshold is 0.25 ng/ml and the sensitivity of the assay is considerably increased compared to the curve A which was obtained without applying the INC process. Indeed, in the case of curve A, the buffer used for the coating and the incubation of $AB_2$ and $AB_3$ was simple PBS-BSA-Tween. Only the reference range of the oFSH was carried out under the same conditions as for curve B, that is to say in PBS-BSA-Tween with addition of serum from a hypophysectomised animal diluted to 1/10th. The comparison of these two curves shows the importance of the INC process for obtaining a very good sensitivity in this assay of the oFSH. These results also show that the efficacy of the INC process is not limited to the assay of animal LH by AB1 and AB2 defined hereinabove, but that it also applies to the assay of another hypophysial hormone, FSH involving other antibodies. The use of the INC medium has made it possible, as in the assay of animal LH and of hLH, to neutralise all non-specific serum interferences and to thus improve considerably the detection threshold and the sensitivity of the assay of oFSH.

* 53 ewe plasmas were assayed for FSH in accordance with the INC process. The results obtained by this technique were correlated with those obtained by a radioimmunological assay:

the correlation coefficient is 0.9759 equation of the straight regression line is Y=0.5856X−0.845 where Y is the concentration of oFSH (ng/ml) measured by ELISA, and X is the concentration of oFSH (ng/ml) measured by RIA.

Finally, it should be noted that high oFSH plasma concentrations (15 to 20 ng/ml) are entirely detectable by eye, without any need for reading apparatus, and are clearly distinguishable from low plasma levels (0.5 to 2 ng/ml). This may permit detection and measuring of the FSH peak secreted before ovulation in completely rustic conditions outside the laboratory.

By means of the detection threshold which it permits in the assay, the INC process affords the possibility of detecting low circulating levels (between 0.25 and 5 ng/ml), which has an obvious physiological value.

EXAMPLE 14

Assay of human LH a—Antibodies used for the assay:

* The first antibody ($AB_1$) is a monoclonal antibody specific to human LH (hLH) marketed by the Pierce Company—reference: 37110. It is a monoclonal antibody of type $IgG_1$, originating from the clone ZMLHZ.
* The second antibody ($AB_2$) is a polyclonal anti-hLH antibody produced in the rabbit and marketed by the company UCB—reference: 1504/001.
* The third antibody ($AB_3$) is a polyclonal antibody marketed by Jackson Laboratories—reference 111-035-003. It is a rabbit anti-IgG antibody linked to peroxidase, produced in the goat.

b—Experimental protocol:

The protocol applied was that in Example 3:

(1) $AB_1$ is prepared in 0.1M carbonate buffer, pH 9.6, at a concentration of 10 μg/ml (or 7.5 μg/ml). 100 μl are distributed per well.

The incubation time is one hour at 37° C. and 18 hours at 4° C.

(2) Washings and coating (cf. Example 3)

(3) Incubation of the samples and of the range: cf. Example 3. The samples to be assayed are diluted 10-fold (or 5-fold) in PBS-BSA-Tween. The hLH range is prepared in PBS-BSA-Tween with addition of serum from a hypophysectomised animal diluted 10-fold. It comprises the following concentrations: 62.5 pg/ml, 125 pg/ml, 250 pg/ml, 500 pg/ml, 1 ng/ml, 2 ng/ml, 4 ng/ml, 8 ng/ml, 40 ng/ml.

(4) Washings—cf. Example 3.

(5) $AB_2$ is prepared at 2.5 μg/ml and pre-incubated in the INC medium in the same way as in Example 3.

(6) Washings.

(7) $AB_3$ is prepared to 1/5000th in INC medium, as in Example 3.

(8) Washings.

(9) Depositing of the substrate (ABTS) and reading of the results after one hour.

c—Results

Figure 21:
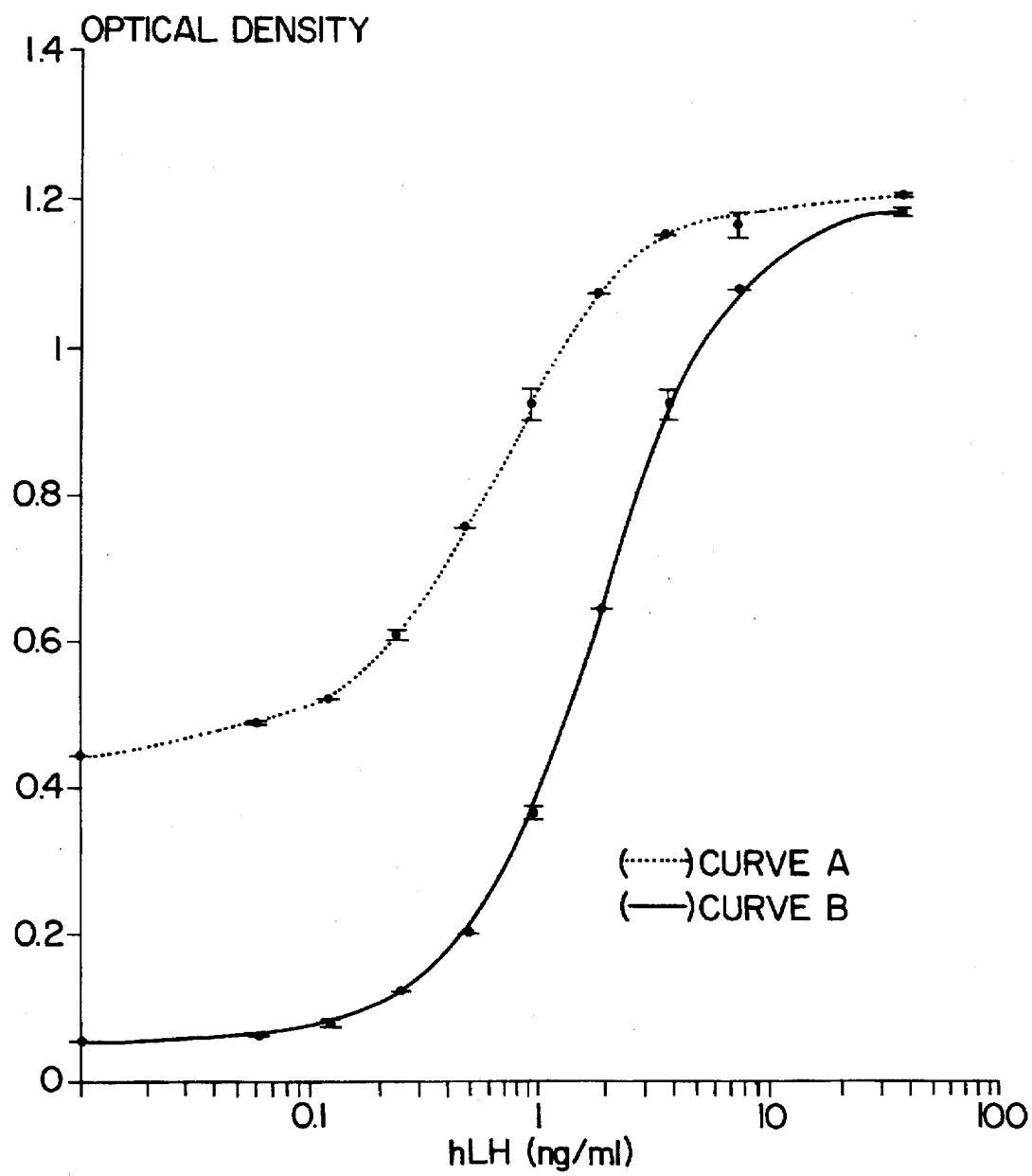
FIG. 21 is a plot of optical density as a function of hLH in assays which included and excluded INC medium.

* FIG. 21 shows the results obtained with an hLH reference range using the INC process in accordance with the protocol hereinabove (curve B) and those obtained with an identical reference range without applying the INC process (curve A). In the latter case, the buffer used for the coating and the incubation of $AB_2$ and $AB_3$ was PBS-BSA-Tween alone. The comparison of the two curves illustrates once again the advantage and the impact of the INC process, which affords a very marked improvement in the sensitivity of the assay and in its detection threshold, by neutralising any non-specific signal due to non-specific serum interferences.

* 20 plasmas from women were assayed for hLH in accordance with the process presented hereinabove. The results obtained by this ELISA technique were correlated with those obtained using the hLH assay kit manufactured by Abbott (immunoenzymo-microparticle system—IMX Abbott):

correlation coefficient is 0.8808 equation of the straight regression line is Y=0.483X+ 0.0986 where Y is the hHL concentration (ng/ml) measured by ELISA, and, X is the hLH concentration (IU/1) measured by the IMX Abbott system).

* Given the absence of any non-specific signal and the great sensitivity of the assay, it will be possible to discriminate between the high values (preovulatory LH peak) giving a green colour, and low values which remain colourless. This "naked eye" interpretation will make it possible to use this process for developing a kit for the detection of the preovulatory LH peak in women at home. It will also be possible to use it for a reliable quantitative assay in the laboratories. These results show that the efficacy of the INC process is not limited to the use of the polyclonal AB1 and AB2 antibodies defined hereinabove in the assay of animal LH, but that it also contributes to improving the assay of another LH (human LH) involving other antibodies (monoclonal anti-hLH AG, PIERCE; polyclonal anti-hLH AB2 produced in rabbit UCB).

As will be apparent from the above, the invention is not in any way limited to those of its modes of implementation, embodiments and applications which have just been described in detail; instead it encompasses all variants thereof which may occur to the person skilled in the art without departing from the scope or from the context of the present invention.

I claim:

1. An immunological assay of hormones in culture media or in biological fluids, said assay employing at least two antibodies specific for the hormone to be assayed, wherein one of said antibodies is fixed to a solid support, and a third antibody linked to a detectably enzyme and binding specifically to one of said specific antibodies, said process comprising the steps of:

pre-incubating separately all of said antibodies and said solid support in a preincubation medium comprising a plasma or a serum having substantially undetectable levels of said hormone, contacting a sample to be tested with said two preincubated specific antibodies, including contacting a second antibody of said two antibodies, which has not been fixed on said solid support and said sample, with said solid support;

contacting said sample with said third antibody; and detecting the presence of said hormone in said sample.

2. An assay according to claim 1, wherein said preincubation medium comprises a serum having substantially undetectable levels of the hormone to be assayed, and wherein said serum is obtained from an animal which has undergone ablation of an endocrine gland which produces said hormone.

3. An assay according to claim 1, wherein said preincubation medium comprises a serum having substantially undetectable levels of hypophysial hormones obtained from a hypophysectomized animal.

4. An assay according to claim 3, wherein said preincubation medium comprises a serum from a hypophysectomized ram.

5. An assay according to claim 2, wherein said preincubation medium is combined with a buffer, and wherein said medium and said buffer are present in a ratio of 1:1.

6. An assay according to claim 1, wherein said at least two antibodies are selected from the group consisting of monoclonal anti-FSH, anti-LH, anti-TSH, anti-GH, anti-ACTH, anti-prolactin, anti-oxytocin, anti-ADH, anti-MSH, anti-hCG and anti-eCG antibodies and polyclonal anti-FSH, anti-LH, anti-TSH, anti-GH, anti-ACTH, anti-prolactin, anti-oxytocin, anti-ADH, anti-MSH, anti-hCG and anti-eCG antibodies.

7. An assay according to claim 1, wherein said first and second specific antibodies are selected from the group consisting of polyclonal anti-ovine LH antibodies produced in rabbit and polyclonal anti-ovine LH antibodies produced in horse, and said third antibody is selected from the group consisting of anti-horse IgG antibody produced by goat and anti-rabbit IgG antibody produced by goat.

8. An assay according to claim 1, wherein one of said at least two specific antibodies is a polyclonal anti-ovine LH antibody produced by rabbit, the second of said at least two antibodies is a polyclonal anti-ovine LH antibody produced by horse, and the third antibody is a anti-horse IgG antibody produced by goat and linked to an enzyme.

9. A reagent for the immunological detection of hormones in animals, comprising:

an anti-hormone antibody which is pre-incubated in a medium having substantially undetectable levels of the hormone to be detected, said medium being a serum or plasma obtained from an animal that has undergone ablation of the endocrine gland which produces said hormone.

10. A kit for the detection of hormones comprising:

two anti-hormone antibodies;

a serum free of the hormone to be detected, said serum being obtained from an animal which has undergone ablation of the endocrine gland which produces said hormone;

an enzyme/antibody conjugate, in which the antibody is a anti-horse IgG produced in goat or a anti-rabbit IgG produced in goat, and which conjugate is pre-incubated in said serum; and a substrate for detection of the enzyme.

11. An immunological assay of hypophysial hormones in culture media or in biological fluids, said assay employing two antibodies specific for the hormone to be assayed, one of said two antibodies being fixed to a solid support, and a third antibody linked to a detectable enzyme and binding specifically to one of said specific antibodies, said assay comprising the steps of:

pre-incubating separately all of said antibodies and said solid support in a preincubation medium comprising a plasma or a serum having substantially undetectable levels of hypophysial hormones derived from an hypophysectomized ram, contacting a sample to be tested with said two preincubated specific antibodies, including contacting a second antibody of said two antibodies, which has not been fixed on said solid support and which is not linked to an enzyme, and said sample, with said solid support;

contacting said sample with said third antibody selected from the group consisting of anti-horse IgG antibody produced by a goat and anti-rabbit IgG antibody produced by a goat; and detecting the presence of said hormone in said sample.

\* \* \* \* \*